US008888720B2

(12) United States Patent
Hudson

(10) Patent No.: US 8,888,720 B2
(45) Date of Patent: Nov. 18, 2014

(54) GREAT TOE DORSIFLEXION DETECTION

(76) Inventor: Stanford P. Hudson, Dallas, TX (US)

( * ) Notice: Subject to any disclaimer, the term of this patent is extended or adjusted under 35 U.S.C. 154(b) by 251 days.

(21) Appl. No.: 13/472,967

(22) Filed: May 16, 2012

(65) Prior Publication Data

US 2012/0232431 A1    Sep. 13, 2012

Related U.S. Application Data

(63) Continuation-in-part of application No. 12/753,553, filed on Apr. 2, 2010, now abandoned.

(51) Int. Cl.
*A61B 5/11* (2006.01)
*A61B 5/00* (2006.01)
*A61B 5/107* (2006.01)

(52) U.S. Cl.
CPC ........... *A61B 5/6833* (2013.01); *A61B 5/411* (2013.01); *A61B 5/1071* (2013.01); *A61B 5/6829* (2013.01); *A61B 2562/12* (2013.01); *A61B 5/1118* (2013.01); *A61B 2562/242* (2013.01); *A61B 5/6828* (2013.01)
USPC ........................................................ 600/595

(58) Field of Classification Search
CPC ...................................... A61B 5/6813–5/6829
USPC ........................................................ 600/595
See application file for complete search history.

(56) References Cited

U.S. PATENT DOCUMENTS

| | | | |
|---|---|---|---|
| 3,234,107 A | 2/1966 | Kaufman et al. | |
| D215,774 S | 10/1969 | Crane | |
| 3,615,222 A | 10/1971 | Mead | |
| 3,972,038 A * | 7/1976 | Fletcher et al. | 340/870.24 |
| D241,173 S | 8/1976 | Corneille | |
| D241,174 S | 8/1976 | Corneille | |
| 4,398,545 A | 8/1983 | Wilson | |
| 4,450,843 A * | 5/1984 | Barney et al. | 600/503 |
| D274,752 S | 7/1984 | Byrne | |
| D275,789 S | 10/1984 | Byrne | |

(Continued)

FOREIGN PATENT DOCUMENTS

| | | |
|---|---|---|
| WO | WO2006105621 | 10/2006 |
| WO | WO2009012298 | 1/2009 |
| WO | WO2009020880 | 2/2009 |
| WO | WO2009136931 | 11/2009 |

OTHER PUBLICATIONS

Home Health Testing; "Body Balance Sleep Hormone Test"; retrieved on Jan. 25, 2010 from www.homehealthtesting.com.

(Continued)

*Primary Examiner* — Sean Dougherty
*Assistant Examiner* — Michael C Stout
(74) *Attorney, Agent, or Firm* — Robert H. Frantz

(57) ABSTRACT

A limb movement biosensor for wearing upon a great toe or other appendage, the wearing upon the great toe being particularly useful for sensing dorsiflexion of the great toe as an indicator of contraction of a wearer's tibialis anterior muscle. A particular configuration of one embodiment allows for extended, multi-night data collection of limb movements by allowing an embedded microcontroller to sleep until movement greater than a pre-determined magnitude is detected by an accelerometer, by recording into memory such detection, while avoiding recording of the actual magnitude value of the detected movement. According to another optional embodiment feature, a light sensor is configured to wake up the processor from a lower power state, such as when a user removes the device from a light-protected package.

17 Claims, 20 Drawing Sheets

(56) References Cited

U.S. PATENT DOCUMENTS

| | | | |
|---|---|---|---|
| D288,716 S | 3/1987 | Covell et al. | |
| 4,813,419 A * | 3/1989 | McConnell | 607/56 |
| D306,645 S | 3/1990 | Parker | |
| 4,922,906 A | 5/1990 | Takeuchi et al. | |
| 5,085,217 A | 2/1992 | Shimizu | |
| 5,218,966 A * | 6/1993 | Yamasawa | 600/490 |
| 5,423,874 A | 6/1995 | D'Alerta | |
| 5,738,219 A | 4/1998 | Arsena et al. | |
| 5,813,766 A * | 9/1998 | Chen | 374/141 |
| 5,913,835 A * | 6/1999 | Naoi et al. | 600/595 |
| 5,964,701 A * | 10/1999 | Asada et al. | 600/300 |
| 6,238,338 B1 * | 5/2001 | DeLuca et al. | 600/300 |
| 6,258,045 B1 | 7/2001 | Ray et al. | |
| 6,306,088 B1 | 10/2001 | Krausman et al. | |
| 6,413,223 B1 * | 7/2002 | Yang et al. | 600/485 |
| D467,348 S | 12/2002 | McMichael et al. | |
| D469,881 S | 2/2003 | Peterson et al. | |
| D470,241 S | 2/2003 | McMichael et al. | |
| D470,595 S | 2/2003 | Crisanti et al. | |
| D470,596 S | 2/2003 | McMichael et al. | |
| D470,597 S | 2/2003 | Peterson et al. | |
| D471,639 S | 3/2003 | McMichael et al. | |
| 6,527,715 B2 | 3/2003 | Balkin et al. | |
| 6,597,944 B1 | 7/2003 | Hadas | |
| D484,988 S | 1/2004 | Peterson et al. | |
| 6,878,121 B2 | 4/2005 | Krausman et al. | |
| 6,886,419 B2 | 5/2005 | Cordery et al. | |
| 6,913,929 B1 | 7/2005 | Da Silva | |
| 6,929,926 B2 | 8/2005 | Marshall et al. | |
| 6,998,250 B2 | 2/2006 | McMichael et al. | |
| 7,008,777 B2 | 3/2006 | Marshall et al. | |
| 7,182,739 B2 | 2/2007 | Kopanic et al. | |
| D550,554 S | 9/2007 | Ledbetter et al. | |
| 7,300,409 B2 | 11/2007 | Kopanic, Jr. et al. | |
| 7,611,669 B1 | 11/2009 | Crisanti et al. | |
| 7,616,988 B2 | 11/2009 | Stahmann et al. | |
| 7,641,116 B2 | 1/2010 | Haas et al. | |
| 7,905,832 B1 | 3/2011 | Lau et al. | |
| 8,337,427 B2 * | 12/2012 | Tsuji et al. | 600/587 |
| 2002/0169381 A1 * | 11/2002 | Asada et al. | 600/485 |
| 2003/0038047 A1 | 2/2003 | Sleva et al. | |
| 2003/0045810 A1 | 3/2003 | Borkowski | |
| 2003/0083559 A1 | 5/2003 | Thompson | |
| 2003/0212316 A1 * | 11/2003 | Leiden et al. | 600/323 |
| 2003/0226695 A1 * | 12/2003 | Mault | 177/25.16 |
| 2005/0042589 A1 | 2/2005 | Hatlestad et al. | |
| 2005/0076908 A1 | 4/2005 | Lee et al. | |
| 2005/0261565 A1 | 11/2005 | Lane et al. | |
| 2006/0074347 A1 | 4/2006 | Eguchi et al. | |
| 2006/0129068 A1 * | 6/2006 | Makosinski et al. | 600/587 |
| 2006/0224072 A1 | 10/2006 | Shennib | |
| 2007/0015976 A1 | 1/2007 | Miesel et al. | |
| 2007/0027388 A1 | 2/2007 | Chou | |
| 2007/0038045 A1 * | 2/2007 | Hayter et al. | 600/317 |
| 2007/0038067 A1 * | 2/2007 | Kandori et al. | 600/409 |
| 2007/0038154 A1 * | 2/2007 | Kandori et al. | 600/595 |
| 2007/0055115 A1 | 3/2007 | Kwok et al. | |
| 2007/0129622 A1 | 6/2007 | Bourget et al. | |
| 2007/0232937 A1 * | 10/2007 | Lam et al. | 600/490 |
| 2008/0077055 A1 | 3/2008 | Allen | |
| 2008/0091090 A1 | 4/2008 | Guillory et al. | |
| 2008/0119707 A1 | 5/2008 | Stafford | |
| 2008/0146956 A1 | 6/2008 | Campuzano | |
| 2008/0156862 A1 | 7/2008 | Haas et al. | |
| 2008/0171915 A1 * | 7/2008 | Kawajiri et al. | 600/300 |
| 2008/0234587 A1 | 9/2008 | Bagha et al. | |
| 2008/0238414 A1 * | 10/2008 | Miyashita et al. | 324/207.22 |
| 2008/0266118 A1 * | 10/2008 | Pierson et al. | 340/573.6 |
| 2008/0283164 A1 * | 11/2008 | Noonan | 150/154 |
| 2008/0287751 A1 * | 11/2008 | Stivoric et al. | 600/301 |
| 2008/0316488 A1 * | 12/2008 | Mao et al. | 356/432 |
| 2009/0018454 A1 * | 1/2009 | Hung | 600/500 |
| 2009/0043224 A1 | 2/2009 | Lundkvist et al. | |
| 2009/0062670 A1 | 3/2009 | Sterling et al. | |
| 2009/0076405 A1 * | 3/2009 | Amurthur et al. | 600/529 |
| 2009/0118648 A1 * | 5/2009 | Kandori et al. | 600/595 |
| 2009/0137921 A1 * | 5/2009 | Kramer et al. | 600/544 |
| 2009/0182204 A1 | 7/2009 | Semler et al. | |
| 2009/0192418 A1 * | 7/2009 | Miyashita et al. | 600/595 |
| 2009/0227888 A1 | 9/2009 | Salmi et al. | |
| 2009/0292194 A1 | 11/2009 | Libbus et al. | |
| 2010/0053862 A1 * | 3/2010 | Pargman | 361/679.01 |
| 2010/0168531 A1 * | 7/2010 | Shaltis et al. | 600/301 |
| 2010/0234716 A1 | 9/2010 | Engel | |
| 2010/0298677 A1 * | 11/2010 | Lu et al. | 600/324 |
| 2010/0324384 A1 * | 12/2010 | Moon et al. | 600/323 |
| 2010/0324389 A1 * | 12/2010 | Moon et al. | 600/324 |
| 2011/0208076 A1 | 8/2011 | Fong et al. | |
| 2011/0270049 A1 | 11/2011 | Katra et al. | |
| 2011/0275907 A1 * | 11/2011 | Inciardi et al. | 600/301 |
| 2011/0313261 A1 | 12/2011 | Bourget et al. | |
| 2012/0029327 A1 * | 2/2012 | Angelides | 600/316 |
| 2012/0083710 A1 * | 4/2012 | Yarden | 600/549 |
| 2012/0179011 A1 * | 7/2012 | Moon et al. | 600/324 |
| 2013/0053656 A1 * | 2/2013 | Mollicone et al. | 600/301 |

OTHER PUBLICATIONS

Sleep Sense; "Movement Sensors"; retrieved on Mar. 31, 2010 from http://www.merchantzoneonline.net/merchants/files/EPC00-0000-027/pdf/12162.pdf.

Merlino, G.; "Restless legs syndrome: diagnosis, epidemiology, classification and consequences"; Retrieved on Mar. 31, 2010 from http://www.springerlink.com/content/r52qn0u58qq28kk5/fulltext.pdf.

Philips Respironics; "PAM-RL objective limb activity monitor"; Retrieved on Mar. 31, 2010 from http://pamrl.respironics.com/PDF/Sales_sheet_rebranded_final_%20lowres.pdf.

Respironics; "PAM-RL Objective Limb Activity Monitor"; retrieved on Mar. 31, 2010 from www.respironics.com.

Shochat; "A KickStrip; A Novel Testing Device for Periodic Limb Movement Disorder".

Wheeless, Clifford R.; "Tibialis anterior", retrieved on Apr. 17, 2012 from Wheeless' Textbook of Orthopaedics at http://www.wheelessonline.com/ortho/tibialis_anterior.

Reference.com; "Tibialis anterior muscle", retrieved on Apr. 17, 2012 from http://www.reference.com/browse/tibialisanterior.

Unknown; "Tibialis Anterior", retrieved on Apr. 17, 2012 from http://www.exrx.net/Muscles/TibialisAnterior.html.

Bernstein, Joseph; "Dosiflexion of the great toe", retrieved on Apr. 17, 2012 from http://www.orthopaedia.com.

Refshauge, Kathryn M.; "Movement detection at the human big toe", Journal of Physiology (1998), 513.1, pp. 307-314.

Anon; "Methid for an on-package measurement system for predicting reliability"; retrieved from http://www.ip.com/pubview/IPCOM00010775D.

Anon;" "FepiBlue"—A wearable febrile/Epilepsy alert wireless sensor belt for a human being"; retrieved from http://priorartdatabase.com/IPCOM/000214729.

Lindsay; "Improved Wearable Sensor Systems" retrieved from http://www.ip.com/pubview/IPCOM00003004.

Elsevier; "World Association of Sleep Medicine" retrieved from www.elsevier.com/locate/sleep.

\* cited by examiner

↙ 104b

A Fill-Out This Side Before Bedtime      Patient Questionnaire

Your Name: _____
(Please Print)

Date: _____  Doctor: _____

Approximate time sensor patches applied to skin:

7:00pm    8:00pm    9:00pm    10:00pm    11:00pm    12:00pm

Other: _____

---

B Fill-Out This Side In The Morning      Patient Questionnaire

Wake-Up Time: _____

Did you wake up during the night? ☐ Yes (list activities below)    ☐ No

| Start Time | End Time | Activity (restroom, reading, drink, etc.) |
|---|---|---|
|  |  |  |
|  |  |  |
|  |  |  |

GREAT TOE DORSIFLEXION DETECTION

This is a continuation-in-part application of application Ser. No. 12/753,553, filed on Apr. 2, 2010, by Stanford P. Hudson. This invention relates to arts and technologies for biosensors, to packaging of biosensors, and to systems for bioinformatics processing.

FIELD OF THE INVENTION

Background of the Invention

Many biosensor systems are well known for use in controlled medical environments such as diagnostics laboratories, hospitals, clinics, and physicians' offices. Such biosensor systems may be large and expensive, and relatively immobile. Their costs of acquisition and operation are recouped by the diagnostic lab, hospital, clinic, or physician by having patients come to the facility where they are located for testing. A "sleep lab" is one such facility where many costly and large sensor systems are used to diagnose sleep disorders while a patient slumbers in a bed at the facility. Bioinformatics functionality such as data collection, data processing, and report generation, are typically provided in an integrated fashion with the biosensor system.

Other large and costly biosensor systems include, but are not limited to, systems for monitoring and studying heart functions, brain functions, and pregnancy-related conditions. The technology and usage models of these systems generally involve acquisition of a costly and somewhat large or immobile sensor collection and bioinformatics processing system, location of the system at a commonly-accessible medical facility, and operation and usage of the system by trained medical staff with patients traveling from their home or residence to the location of the medical facility in order to be close enough to the system for sensor application and data collection.

SUMMARY OF THE INVENTION

A limb movement biosensor is described for wearing upon a great toe or other appendage, the wearing upon the great toe being particularly useful for sensing dorsiflexion of the great toe as an indicator of contraction of a wearer's tibialis anterior muscle. A particular configuration of one embodiment allows for extended, multi-night data collection of limb movements by allowing an embedded microcontroller to sleep until movement greater than a pre-determined magnitude is detected by an accelerometer, by recording into memory such detection, while avoiding recording of the actual magnitude value of the detected movement. According to another optional embodiment feature, a light sensor is configured to wake up the processor from a lower power state, such as when a user removes the device from a light-protected package.

BRIEF DESCRIPTION OF THE DRAWINGS

The following detailed description when taken in conjunction with the figures presented herein provide a complete disclosure of the invention.

FIG. 5 illustrates an example patient questionnaire.

DESCRIPTION OF THE INVENTION

Figure 1:
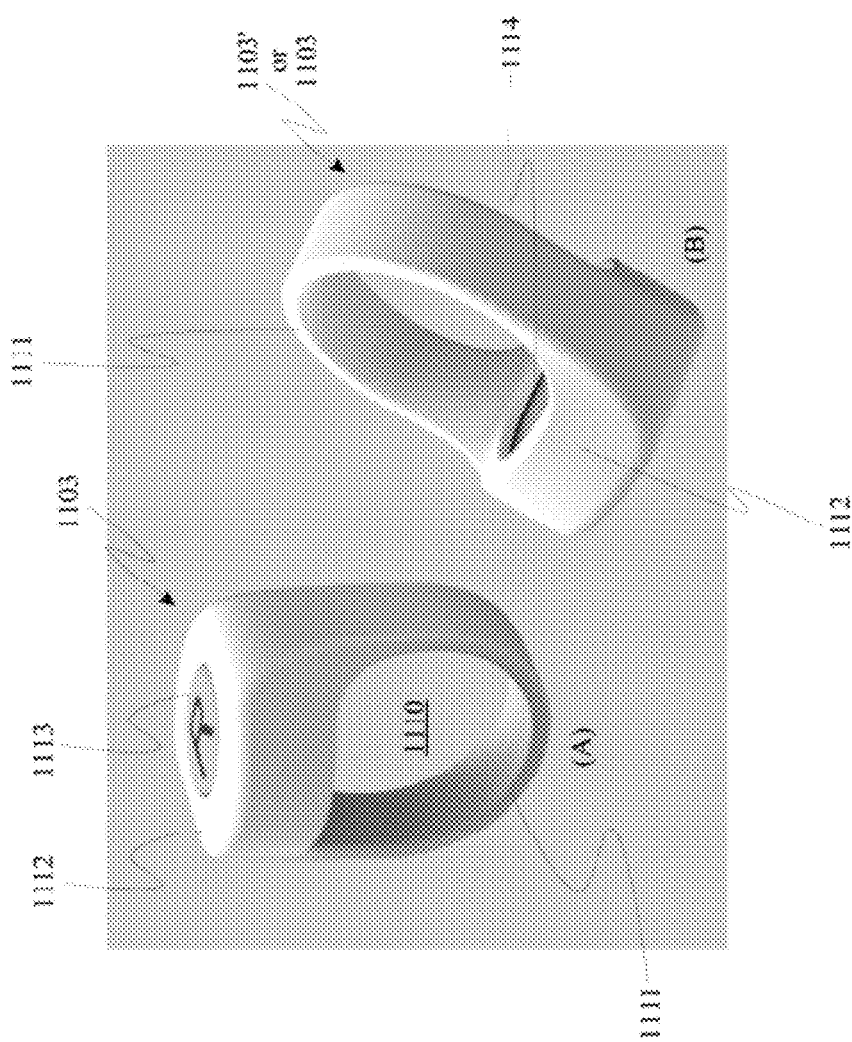
FIG. 1 illustrates an external view of a biosensor for wearing on a big toe according to the present invention.

The inventors of the present invention and related invention have recognized that the aforementioned technology and usage models of common biosensor and bioinformatics systems that generally involve acquisition of a costly and somewhat large or immobile sensor collection and bioinformatics processing system, location of the system at a commonly-accessible medical facility, and operation and usage of the system by trained medical staff with patients traveling from their home or residence to the location of the medical facility in order to be close enough to the system for sensor application and data collection, is problematic in that it contributes to several problems in the art:

(a) it is inconvenient for many patients to travel to the location of the system;
(b) it can be expensive for non-ambulatory patients to travel to the location of the system;
(c) it is expensive to train and maintain staff skills for direct operation of complicated and advanced biosensor and bioinformatics systems; and
(d) the foregoing costs and expenses may conspire to tempt a medical professional to over-use such a system (e.g. prescribe use for the system when not clearly medically indicated or justified) in order to recoup the cost of the system and the specially-trained staff.

Having recognized these problems in the art, the inventors set about to develop new biosensor technologies and bioinformatics processing usage models which would:

(a) provide for increased patient convenience by providing patients with a biosensor which is suitable for application and use in a home environment by an untrained person such as the actual patient or a lay caregiver;

(b) through use of the at-home sensor of (a), eliminates the requirement for non-ambulatory patients to travel to the location of the bioinformatics processing system;

(c) reduces the cost of bioinformatics processing and sensor application by eliminating the need for physicians, clinics, labs, and hospitals to maintain specially trained staff through providing bioinformatics processing in a service model, preferably remote to the actual prescribing physicians' offices, clinics, labs, and hospitals;

(d) thereby removing temptations to a medical professional to over-use such a system due to elimination of large outlays to acquire a biosensor and bioinformatics system, and elimination of keeping specially-trained personnel on staff.

The Related Invention

In an earlier design, the present inventors devised a biosensor kit and method for use thereof for at-home collection of biosensor data having one or more biosensors with a top patch-shaped layer affixed to a bottom patch-shaped layer, the layers being made of cushioning sheet material, such as medical foam tape, and having a biosensor circuit disposed between the layers such that the top layer and bottom layer form a protective, dual-mode encapsulation of the biosensor circuit for cushioning against the skin or a garment of a wearer, and for protection of the biosensor circuit during shipment and handling. The kit further includes a carrier card of suitable size to receive and carry the biosensors in a substantially flat, co-planar arrangement in a substantially flat envelope or pouch for shipment through flat piece mail or postal service. The cushioning sheet material of the biosensor layers is sufficient packing material to avoid requiring additional protective packing material.

This earlier design and method of processing the data associated therewith will be described in the following paragraphs, whereas it provides a more complete understanding of the present invention and its further improvements not only over the prior art, but also over this predecessor design. The earlier design is the subject of the related patent application, from which the present patent application is a continuation-in-part.

The aforementioned advantages of the earlier design, and other advantages, will be apparent in the following paragraphs. In the exemplary embodiments, the inventors provide methods, materials, and processes suitable for use in the sleep disorder study, diagnosis and treatment medical fields, especially studies which measure periodic limb movements. However, the invention may be equally beneficial to other neurological practices, as well as to other fields of medicine, such as cardiology, obstetrics, etc., which benefit from the use of biosensors and bioinformatics. It should be noted that no statement contained herein should be taken as a statement of use for medical purposes without proper regulatory review or approval, but instead such statements of are potential utility.

Overview of the Biosensor and Bioinformatics System and Usage Models of the Earlier Design.

Figure 10:
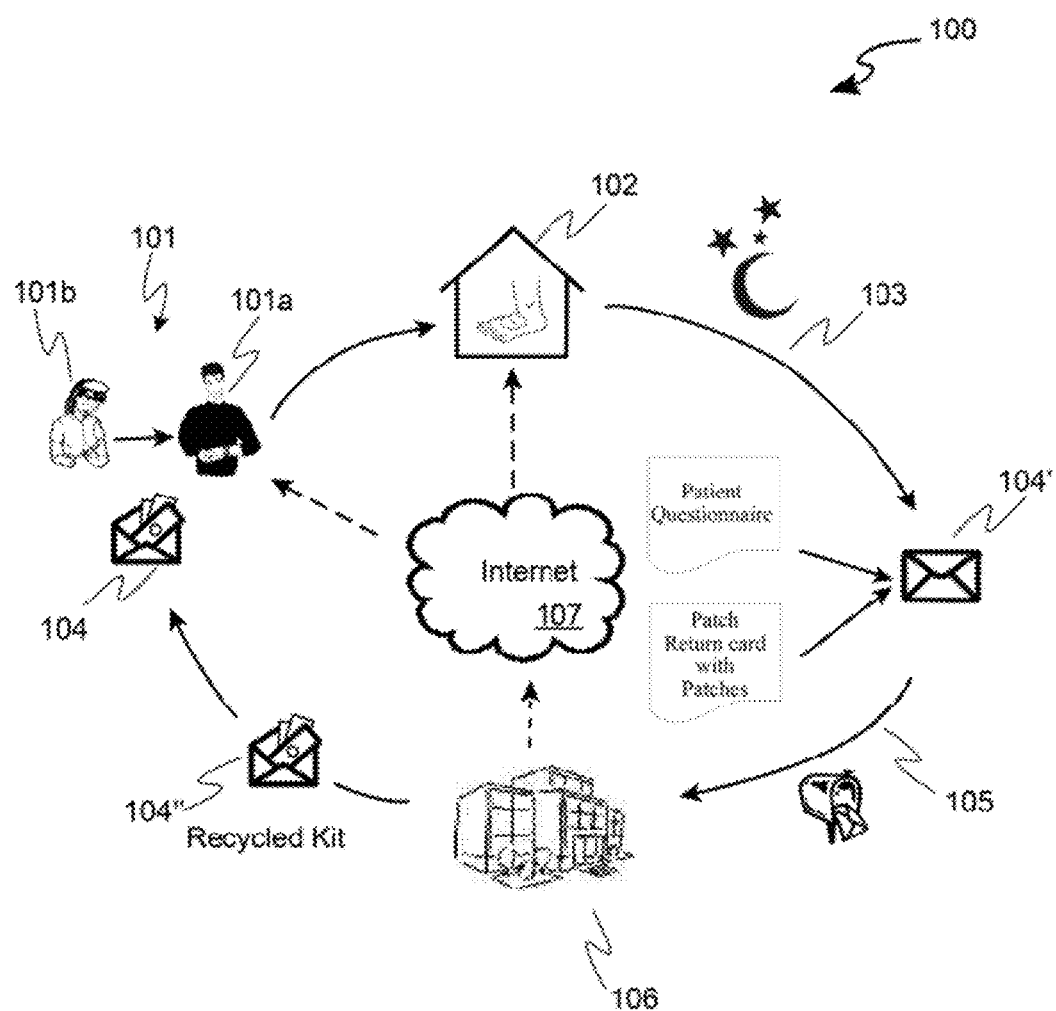
FIG. 10 shows an overview of the new biosensor and bioinformatics system and the model for usage.

Turning to FIG. 10, an overview of the new biosensor and bioinformatics system and the model for usage (100) is shown. When a patient (101a) visits a medical facility (101) such as a physician's office, laboratory, clinic, or hospital, for initiation of biosensor-based testing and diagnosis, he or she is provided a fresh "take home" biosensor kit (104) by a staff member (101b) at the medical facility. Because of the design of the biosensor kit to be applied and used by non-medical personnel, such as by the patient himself or herself, the staff member (101b) need not be specially trained in application and use of the biosensor, nor specially trained in the operation of the bioinformatics processing system associated with the particular test or diagnostic procedure. In our example embodiment, the patient is given a take-home kit containing a number of components, including, but not limited, to one or more self-adhesive limb movement biosensor "patches" which will be described in greater detail in the following paragraphs.

The patient then returns to his or her home or residence (102), whereby the patient receives instructions on the use and application of the sensor(s), and may be required to complete certain questions on a questionnaire, such as time of application and activation of the biosensor and "vital conditions" of the patient at such time (temperature, diet, pain levels, etc.). Next, the patient activates and applies the biosensor for a period of time or throughout an activity (103), such as overnight while sleeping in the example embodiment of an limb movement biosensor.

At the conclusion of the activity or sensor operation period (103), the patient then removes the biosensor(s), applies them to a biosensor carrier card to defeat an adhesive surface, and preferably completes the rest of the questionnaire, such as recording time of biosensor removal, and patient "vitals". These are then placed in a "return" package (104') included in the original fresh kit (104), and shipped via postal or courier service (105) to a bioinformatics data processing center (106). The "return" package is preferably self-addressed to the bioinformatics data processing center, and is provided with pre-paid, collect-on-delivery, or addressee-charged postage or courier charges. While the term "return" is used here because, from the patient's perspective, it may appear that he or she is returning the sensors to the lab or medical facility, but in reality, he or she is forwarding the used sensors and information to the bioinformatics processing center.

Upon receipt of the used kit (104'), the bioinformatics data processing center removes the questionnaire and biosensors from the return card and uploads or reads the biosensor data from the units into a computer equipped with suitable bioinformatics programs. In the exemplary embodiment, the bioinformatics data processing center is equipped with suitable computers and programs to analyze limb movement sensor data and to produce one or more graphic reports for assisting a physician in the diagnosis and treatment of various sleep movement disorders, muscular diseases, or neurological syndromes.

At this point, depending on the cost of the sensors and the materials employed in the sensors, the biosensor units may be discarded, or they may be erased and "cleared" to a "fresh" state, placed in a recycled "fresh" kit (104"), and shipped to a medical facility where the entire cycle (100) may be repeated.

It is important to note that this process (100) is enhanced for cost and usage by one or more features of the invention, described in more detail in the following paragraphs, which may be embodied together or in sub-combinations:

(a) medical facility cost is reduced by providing a biosensor which is easy enough to use by a patient without instructions beyond a printed instruction sheet or included video media (DVD, Thumbdrive, etc.);

(b) shipping costs are reduced by providing a biosensor having a weight and thickness which allows for mailing or shipping in a flat envelope without a special surcharge;

(c) shipping costs are further reduced by producing a biosensor using materials which, in a first manner of usage, act as a comfortable, hygienic, hypo-allergenic, pliable self-adhesive patch, and which, in a second manner of usage, act as sufficient impact absorption to protect sensitive electronics such as accelerometers, batteries, electrical pickups, temperature sensors, and strain gauges, during normal shipping and handling, thereby reducing or eliminating the need for supplemental impact packaging such as foam, air bags, or bubble wrap; and (d) bioinformatics processing is handled remotely from the medical facility, providing reports via electronic communications such as the Internet, email, etc., thereby reducing the equipment cost, size, and training expenses of having the bioinformatics co-located with the biosensors at the medical facility.

These process improvements and efficiencies are directly enabled and provided by certain structural and operational aspects of the invention's several embodiment aspects which will be described in full detail in subsequent paragraphs.

Biosensor Kit of the Earlier Design.

Figure 2:
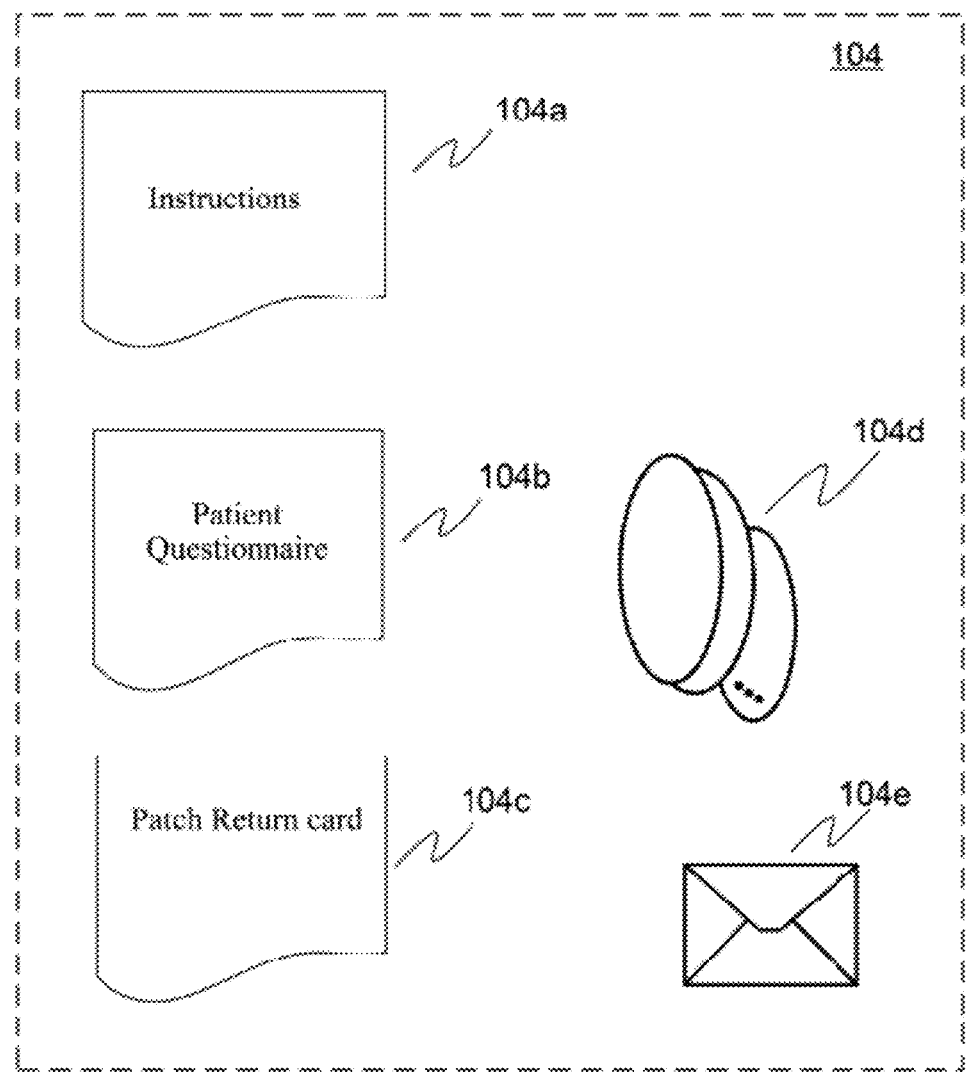
FIG. 2 provides an illustration of a biosensor kit according to at least one embodiment of the related invention.

FIG. 2 provides an illustration of a biosensor kit (104) according to at least one embodiment of the related invention. This kit is exemplary only, as the actual contents of other kits for other types of medical studies may include more or less components without departing from the spirit and scope of the related and present inventions.

The biosensor kit preferably includes instructions (104a) for the non-medically-trained user, such as a patient or lay caregiver, a questionnaire or data collection form (104b), one or more biosensors (104d), and a return card (104c) for acting as a carrier of the self-adhesive biosensors. Also included in the exemplary embodiment is a postage-paid pre-addressed envelope (104e) for sending the used biosensors and completed questionnaire to the bioinformatics processing center.

Exemplary Biosensor of the Earlier Design.

Figure 3:
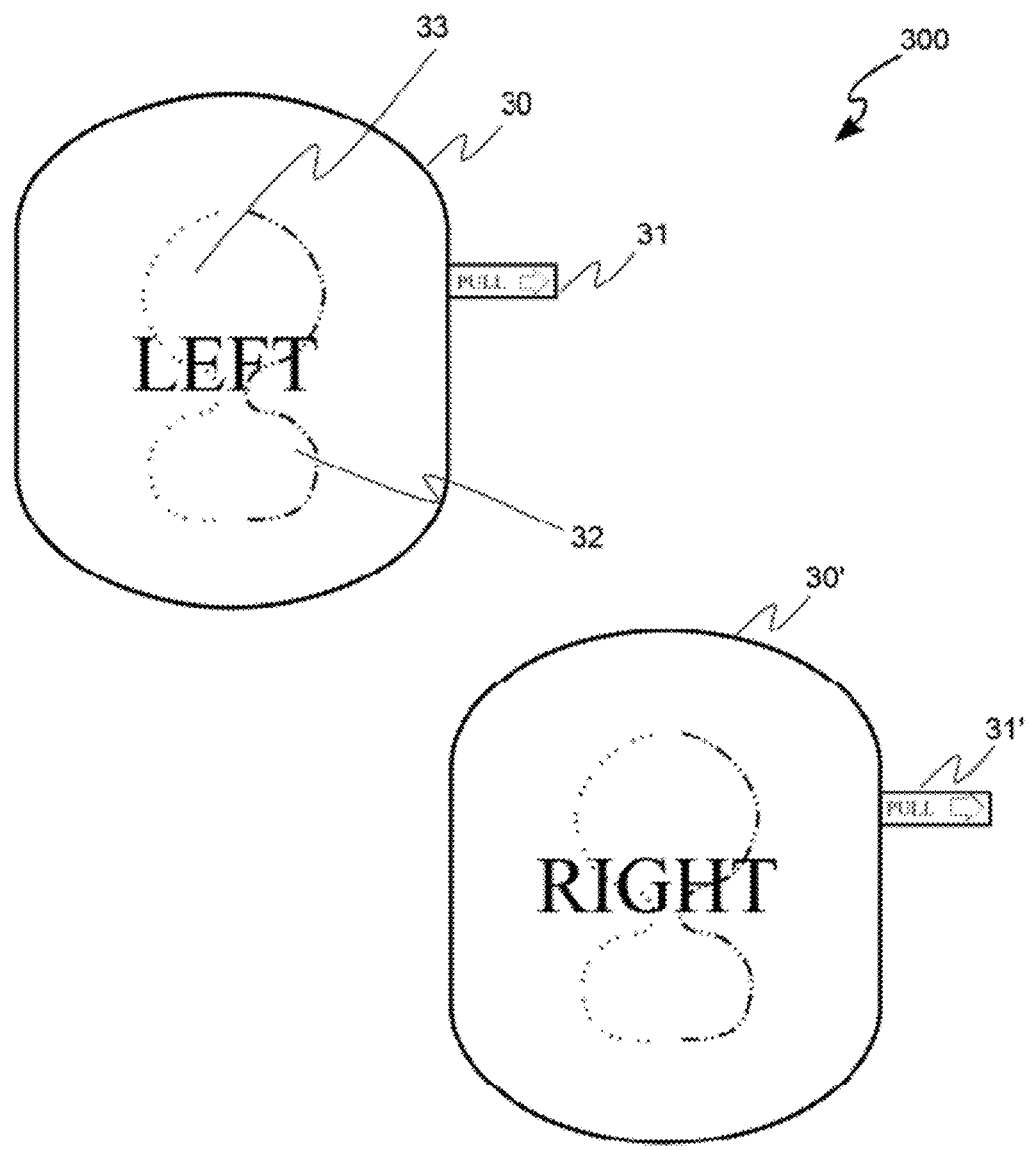
FIG. 3 shows a top-view of a pair of limb movement biosensors.

As already stated, an exemplary embodiment is a limb movement sensor system which may find utility for the measurement, diagnosis, and treatment of sleep disorders such as Periodic Limb Movement Disorder (PLMD). FIG. 3 shows a top-view of a pair of such biosensors (300).

In this embodiment, each "patch" (30, 30') has a battery isolation strip (31, 31') which prevents an internal battery from completing a circuit to an internal biosensor circuit utilizing an accelerometer to measure and collect limb movement data. The battery and circuit are fully enclosed (32) in the patches in a package which may be referred to as a "blister" pack, described in more detail in the following paragraphs.

To activate each sensor, the user must only pull the battery isolation strip out of the patch, thereby completing a conductive path from the battery to the biosensor circuit. Alternatively, for extremely low power circuits or short-duration studies, the battery may be engaged continuously. Or, a switch may be employed in place of the battery isolation strips.

To apply the biosensors, a release paper is removed from the bottom surface (not shown), exposing a self-adhesive surface for adhering the patch to a patient's foot, leg, forearm, or hand, for example.

Method of Manufacture of Biosensor of the Earlier Design.

Figure 4:
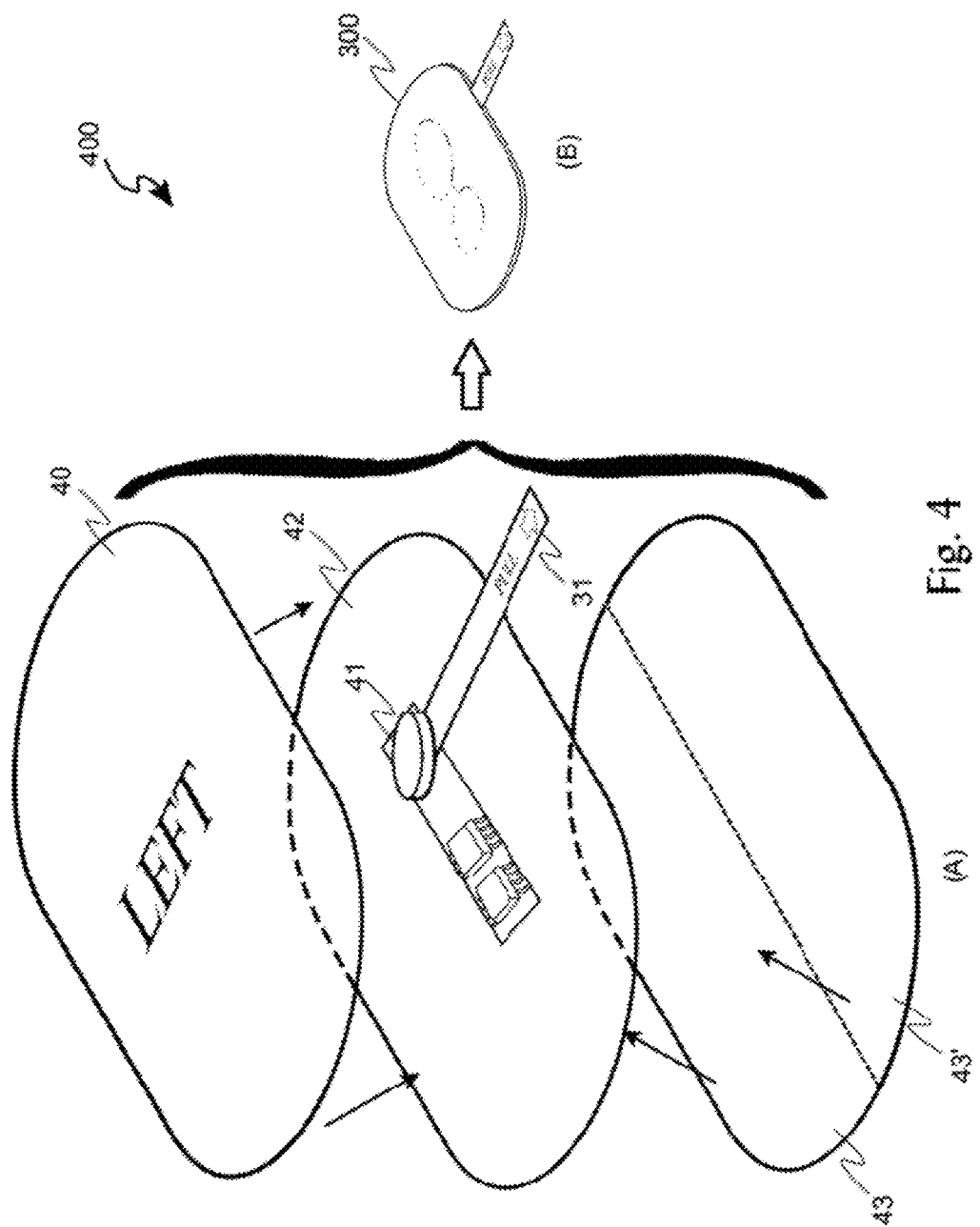
FIG. 4 illustrates a method of manufacture of a biosensor in at least one embodiment of the invention.

According to another aspect of at least one embodiment of the related invention, a biosensor is manufactured by cutting or forming two patch-shaped pieces (40, 42) of self-adhesive medical foam tape, such as 3M™ No. 9777-L PVC surgical foam tape or similar hypo-allergenic, hygienic foam tape, as illustrated in FIG. 4a. Alternatively, medical-grade cushioning sheet material may be used as well, such as cast padding or fibrous foot corn patch material, and suitable adhesive may be used as appropriate to affix the layers together and to the patient.

A biosensor circuit board with battery (41) is preferably disposed between the top patch layer (40) and the bottom patch layer (42) by adhering the top layer to the bottom layer, thereby by capturing the circuit board "sandwiched" between the top and bottom layers but sealed around the circuit board, thus forming a padded blister packaging for the circuit board. In the exemplary embodiment, a battery isolation strip (31) extends from the edge of the pair of layers of the patch in order to allow the user to pull the strip out to activate the biosensor circuit board. Also according to this exemplary embodiment, the biosensor board may be constructed using a flexible printed circuit board ("flex circuit") to enhance comfort of the patch when worn by a user, and to promote conformance of the patch to non-planar surfaces of a patient's body, such as the top of the arch of a foot.

In this exemplary embodiment, release paper (43, 43') is provided on the bottom surface of the bottom layer (42), which, when removed by the lay caregiver or the patient, exposes an adhesive for affixing the patch to a body part, such as the top of a foot.

The assembled patch (300) as shown in FIG. 4b resembles a thick, flexible, impact-absorbing patch with self-adhesive release paper on the bottom side, with a battery activation strip extending from one edge, and potentially with lump or blister in the center (33 in FIG. 3) of the patch. The foam or cushioning sheet material used in the construction of the patch layers acts as a carrier to hold the circuit to the patient's body part, but also serves a second function to shield the sensitive biosensor circuit from impacts during mailing or shipping of the kit to the bioinformatics processing center. By integrating the packing material for the biosensor into the construct of the biosensor itself, costs are reduced by eliminating need for additional packing material in the return envelope, such as bubble wrap, and by reducing the thickness of the return envelope which leads to lower postage costs.

Patient Data Collection of the Related Invention.

In many manners of usage of biosensors according to the related invention, some information may be needed from the patient or lay caregiver about the application and activation of the biosensor, and potentially vital statistics about the patient, such as date and time of activation, patient's name, and details of nighttime activities, as in the example embodiment for limb movement studies, shown in FIG. 104b. A portion of the questionnaire may be completed prior to or at the time of activation and application of the biosensor, and a portion of the questionnaire may be completed upon removal of the biosensor, such as a before bedtime and upon waking, respectively, in the example sleep study embodiment.

Biosensor Return Carrier Card of the Earlier Design.

Figure 6:
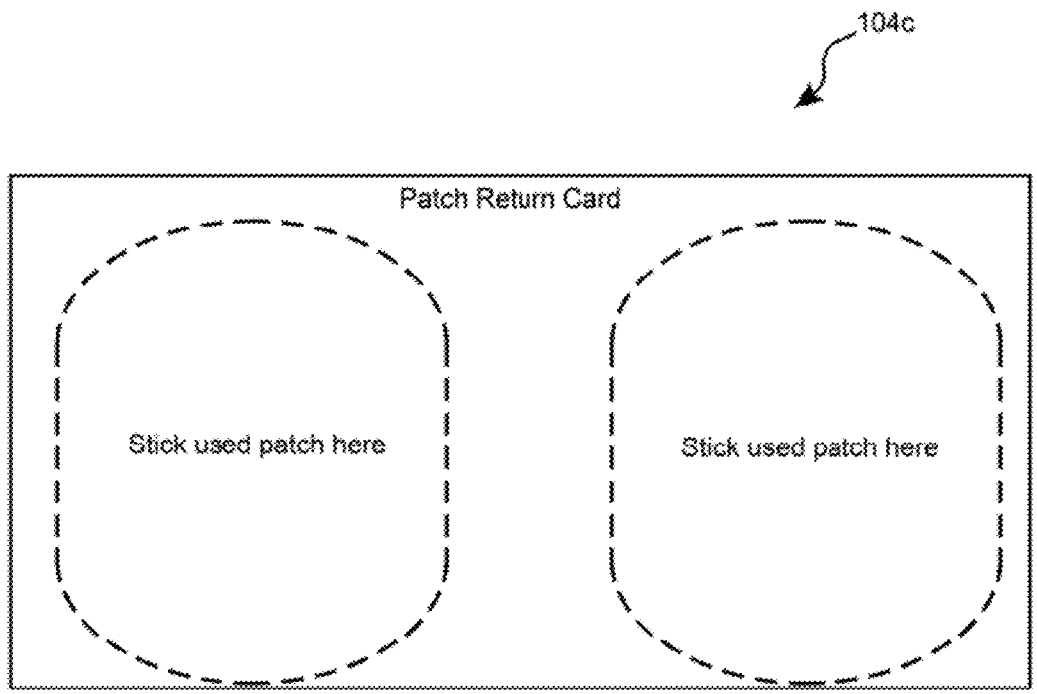
FIG. 6 illustrates an example biosensor shipping carrier card.

According to another aspect of one embodiment of the related invention, the "return" package includes a biosensor return carrier card (104c), as shown in FIG. 6, upon which the user may affix the removed and used biosensors using the same self-adhesive bottom surface that was previously used to affix the biosensors to the body part. This card serves several functions in this embodiment, including:

(a) it maintains the relatively flat biosensor patches in a co-planar arrangement for flat packaging into the pre-addressed envelop in order to minimize thickness and postage of the filled envelop;

(b) it organizes the contents of the return package to allow quick and efficient inbound handling at the bioinformatics processing center; and (c) it occupies the sticky self-adhesive surfaces of the patches after they were removed from the body part in order to keep them from sticking to the inside of the envelop or to each other.

Biosensor Logical Processes of the Earlier Design.

Figure 7:
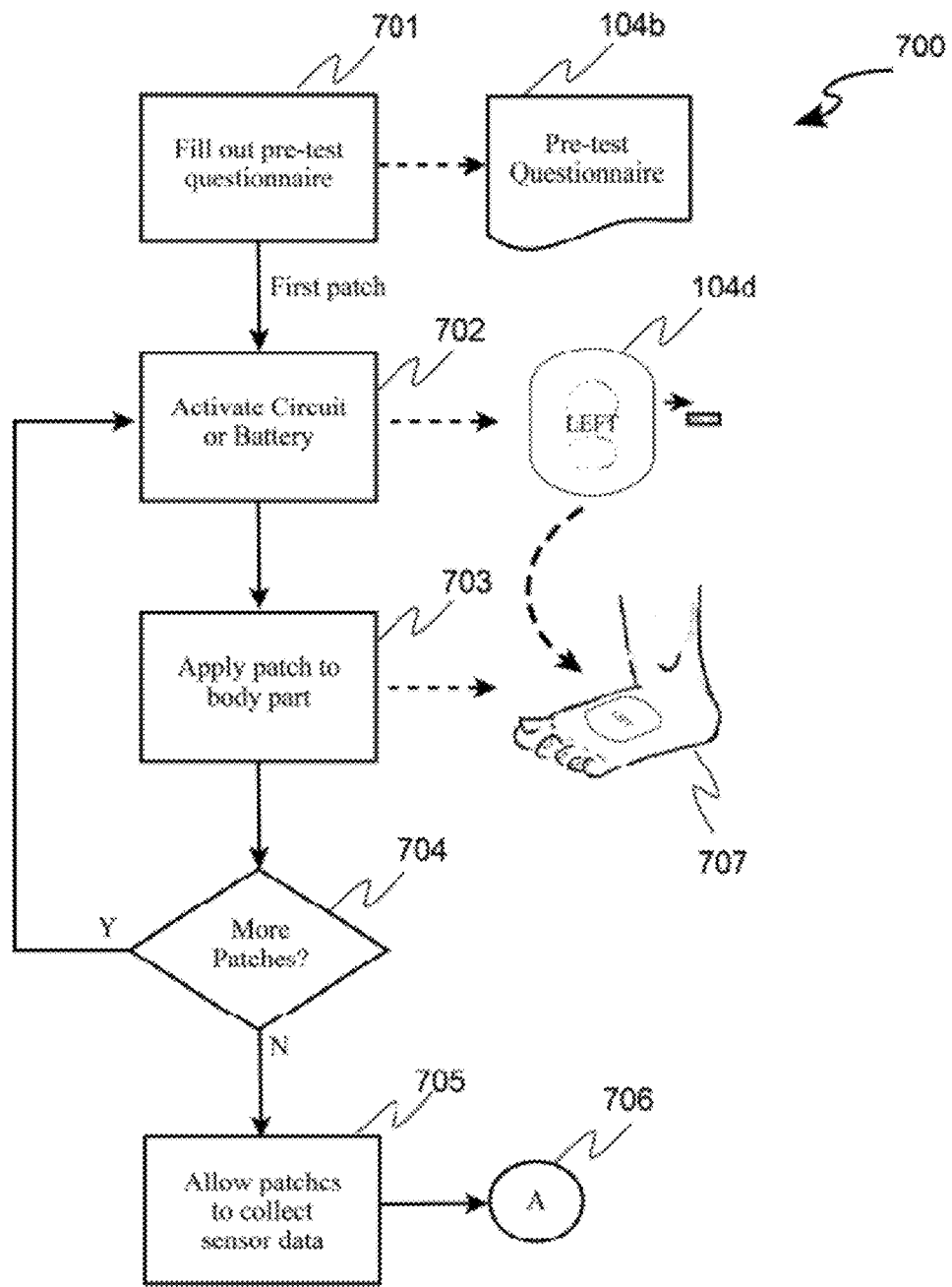
FIGS. 7, 8 and 9 set forth logical processes according to at least one embodiment of the invention for end-user usage of the biosensor system.

Turning to FIG. 7, a logical process (700) for a manner of usage of at least one embodiment according to the related invention is shown. In the example sleep study embodiment, the patient completes a bedtime portion of the questionnaire (701), and then activates a first biosensor patch (702) by, for example, removing the battery isolation strip, or alternatively pressing a switch or button. The first biosensor patch is then applied to a body part (703), such as by removing a release paper to expose the bottom adhesive layer and affixing the first patch to a first body part, such as the top of a first foot. If more patches are to be employed (704), then the activation (702) and application (703) steps are repeated until all patches have been activated and applied.

Then, the patient performs an activity for a period of time (705), such as sleeping normally in his or her own bed overnight (rather than in a hospital bed in a sleep lab) in the example embodiment of a limb movement biosensor system.

Figure 8:
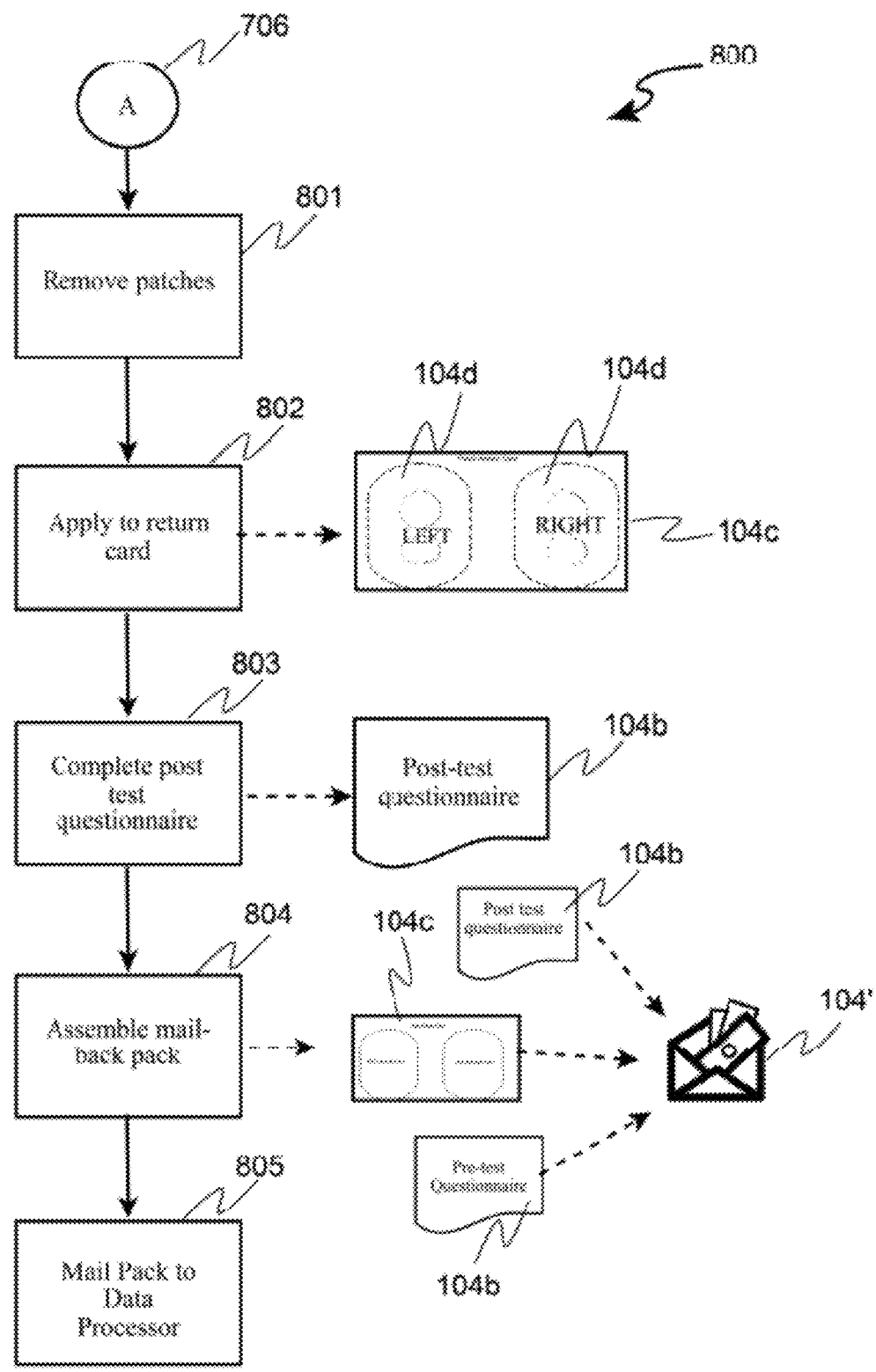

Following completion of the testing or monitoring activity and/or period, the logical process continues (706) as shown (800) in FIG. 8. The user or lay caregiver removes the biosensor patches (801), affixes them to the biosensor carrier card (802), and optionally completes a post-test portion of a patient questionnaire, such as time of patch removal or time of waking. Then, the end-user assembles (804) the mail-back "return" pack as set forth in the user instructions, placing (805) them in the postal service or other courier service for delivery to the bioinformatics processing center, as illustrated more generally in FIG. 1.

Figure 9:
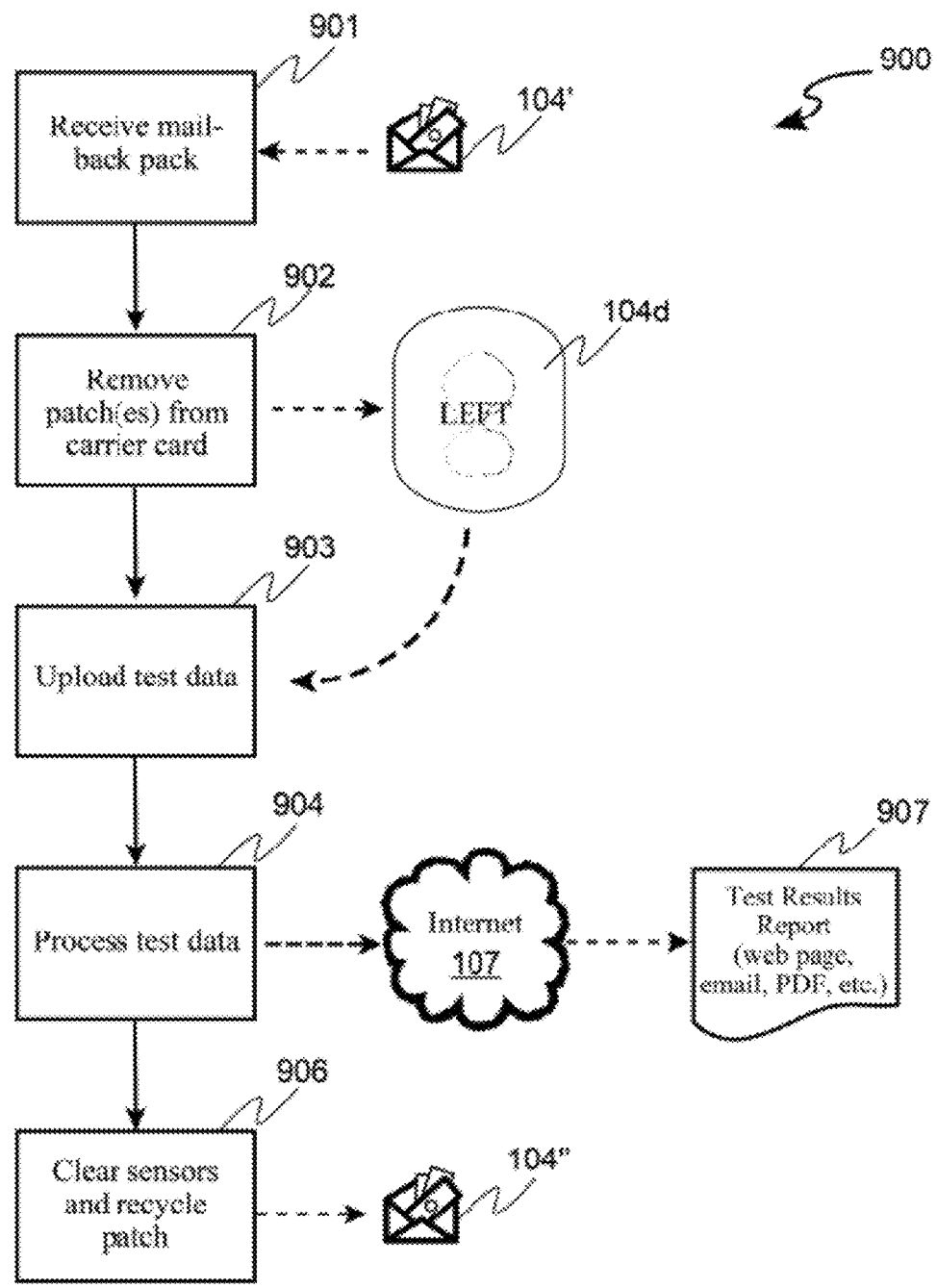

Turning to FIG. 9, a logical process (900) according to at least one embodiment of the related invention is shown for bioinformatics data processing and manner of usage of the used biosensors. The mail-back pack (104') is received (901) by the bioinformatics processing center, and the patches are removed (902) from the pack. Test data is then uploaded (903) from each patch, such as by short range wireless communications such as BlueTooth™ or Radio Frequency Identification (RFID), or by a wired connection such as Universal Serial Bus (USB). The uploaded data is then processed (904) by a computer and one or more computer programs at the bioinformatics processing center (106), and results and reports (907) from which are then preferably made available via an electronic storage medium such as a secure web page on a web server connected to the Internet (107), by secure email, by secure email attachment, or similar, to the physician or medical facility (101), and optionally to the patient at home (102). The reports and results are then available remotely and conveniently to the physician's and/or their staff, and optionally to the patient or the patient's lay caregiver.

According to this example embodiment, the sensors are then "recycled" (906) by clearing their memories, replacing the battery isolation strip, and optionally replacing the battery, in preparation for sending them to another medical facility for re-use. In the example embodiment in which medical surgical foam tape is used for the layers of the biosensor patch, many of these foam tapes are produced on a spool or roll such that their adhesive does not adhere permanently to the top side of the foam. This non-permanent adhesion "to itself" allows for the tape to be removed from the roll, of course. In such an embodiment, it also allows the two layers of the patch assembly to be easily separated, revealing the biosensor circuit board and the battery. When the circuit board is exposed, the battery may be serviced by installing a battery isolation strip, and optionally by replacing the battery. Then, the circuit can be readily assembled into fresh patch layers of medical foam tape.

Limb Movement Biosensor Example Embodiment Details of the Earlier Design.

In the foregoing example embodiments of the related invention, sensors were described to illustrate at least one manner of usage of the invention. The following paragraphs provide additional details of an actual prototype system produced and tested by the inventors. This prototype was used to prove and perfect the concept, and in no manner represents the limits of the scope of the related invention.

General Description of the Related Invention.

The periodic leg movement sensor device is designed to sense and log periodic leg movements while the user is sleeping. The sensor device is enclosed in a patch that is attached to the user's skin via adhesive. Alternatively, the patch may be affixed to a conforming garment worn by the user, such as a sock or bandage. After use, data is downloaded from the sensor device to a computer for post-processing and analysis. The typical system is comprised of two (2) sensor devices (patches) that are worn on the left and right foot of the user.

System Components of the Related Invention.

The periodic leg movement sensor device circuit is, according to at least one embodiment of the related invention, comprised of a microprocessor, a tri-axis accelerometer, a non-volatile memory, a battery, and an activation switch. An analog-to-digital (ADC) peripheral internal to the microprocessor is used to sample the outputs from the accelerometer. Preferably, all three axis outputs from the accelerometer are used (X, Y and Z). However, in some embodiments, fewer axes may be suitable and sufficient depending on the application.

The sensor activation switch is, according to one embodiment, provided in the form of a non-conductive battery isolation strip is inserted between a metal plate and a conductor such as a printed circuit board pad or a solder blob to break the connection between a terminal of the battery and the rest of the biosensor circuit. While the connection is broken, no battery power is applied to the circuit.

System Activation of the Earlier Design.

To activate the biosensor of the earlier design, the user removes the non-conductive battery isolation strip when the sensor is ready to be used. Removal of the isolation strip allows the metal plate to conductively contact the PCB pad or solder blob, thereby completing the circuit from the battery to the biosensor circuit, allowing current to flow to the biosensor circuit from the battery, thus powering (activating) the biosensor. The user then applies the biosensor (enclosed in the patch) to the top of the foot.

Data Collection Method of the Earlier Design.

After activation, the biosensor begins collecting data by sampling outputs by a microprocessor from an integrated accelerometer (via the ADC), for example, at 8 samples per second in one embodiment. Also according to this particular embodiment, there is no filtering or averaging of data. All three outputs are summed together for each sample by the microprocessor, and the absolute difference between the previous summation and the current summation is then compared with a threshold. If exceeded, then it is considered movement. The memory contains 512 bytes. Each bit represents 10 seconds for a total recording time of over 11 hours. If movement occurred within a particular 10-second period, then the bit is set for that period. When a movement occurs, the system will not record any further movements until no movement has occurred for at least 5 seconds. Alternate embodiments may use different filtering, averaging, summation, and recording schemes.

The biosensor continues, according to one embodiment, to collect data and store data until either (1) the non-volatile memory is full, or (2) the system is powered off.

Data Download Method of the Related Invention.

Data is downloaded from the biosensor to a computer, such as a Personal Computer (PC) via a serial connection. The biosensor outputs only the contiguous non-FF non-volatile memory values starting at address zero in one embodiment, in which the output is in two-digit hexadecimal format. Hyper-Terminal™ is used to download the HEX data to a text file, for example.

Data Processing and Analysis Methods of the Related Invention.

A software program running on the PC extracts the data from the downloaded text file and, using a number of developed algorithms, produces a text file containing:
1. the decimal version of the hexadecimal data;
2. valid leg movements (LMs);
3. valid periodic leg movements (PLMs); and
4. statistics including, but not limited in all embodiments to, total sleep time, LM index (e.g. average number of leg movements per hour of sleep), PLM index (e.g. number of periodic leg movements per hour of sleep), and number of LMs, number of PLMs.

According to our exemplary embodiment, a valid leg movement is determined to be a movement that lasts between 0.5 seconds and 5 seconds. And, a valid PLM sequence is comprised of four or more consecutive valid leg movements which are 5 to 90 seconds apart.

Optionally, one or more histograms may be graphically produced representing any or all of this information, as well, such as by using spreadsheet is used to plot the various information.

Details of the Embodiments According to the Present Invention

Introduction.

The following paragraphs describe the features and capabilities of an improved design of the biosensor related to the earlier design which was described in the foregoing paragraphs.

Additional Unmet Needs in the Art Discovered and Recognized.

After further research by the present inventor, additional unmet needs in the art were recognized and addressed in a newer design of the biosensor. It was concluded that the improved biosensor needed to measure and store multiple night's worth of sleep movement data rather than a single night. This is due to variability of the amount of movement that can occur from night-to-night. Five (5) nights of data collection is sufficient time to obtain this data and produce an average score that is a more reliable indicator of the movement profile for the patient.

The "multi-night" data storage capability meant that the patch needed to be removable and reapplied multiple times so that a subject would not have to wear the patch during the day. Pressure adhesives do not work well for such use cases. Hydrogel adhesives are more conducive to this type of usage, however they are highly susceptible to drying out if they are not placed onto the release liner and protected during times of non-use. And, due to their stronger adhesive properties, removal of the patch can be problematic for older patients or diabetics with thinning of the skin. Therefore, it was decided to move away from the adhesive patch and to mount the device into a removal band that can be worn by the patient.

An additional issue is the reliability and high-cost of a custom activation pull-tab spring switch. It was also difficult to reliably activate both sensors simultaneously. To solve these issues, a light activation device was invented which could activate the product. With the new product, the devices are kept in a light-proof bag or package until use. Upon opening the bag by the user, light exposure will activate the sensors simultaneously and automatically without any intervention from the user.

Due to the multi-night data storage requirement, an external non-volatile memory was added to allow for 120 hours of recording time. And, a new low-power accelerometer was added to the device hardware which offloads some of the accelerometer processing onto hardware. As a result of design changes, improvements and further innovations, the newer biosensor provides several additional features and benefits, including but not limited to:

up to 120-hour recording time (5 nights)

a medical-grade silicon rubber housing (great toe band) replaces the adhesive patch light activation replaces the electro-mechanical pull-tab activation simultaneous activation of left foot and right foot devices is provided larger external non-volatile memory is provided low-power accelerometer allows the microprocessor to sleep in low power mode for more of the data collection time smaller electronics foot-print with smaller battery yields smaller biosensor overall power consumption is reduced significantly Product Method of Use.

Figure 11:
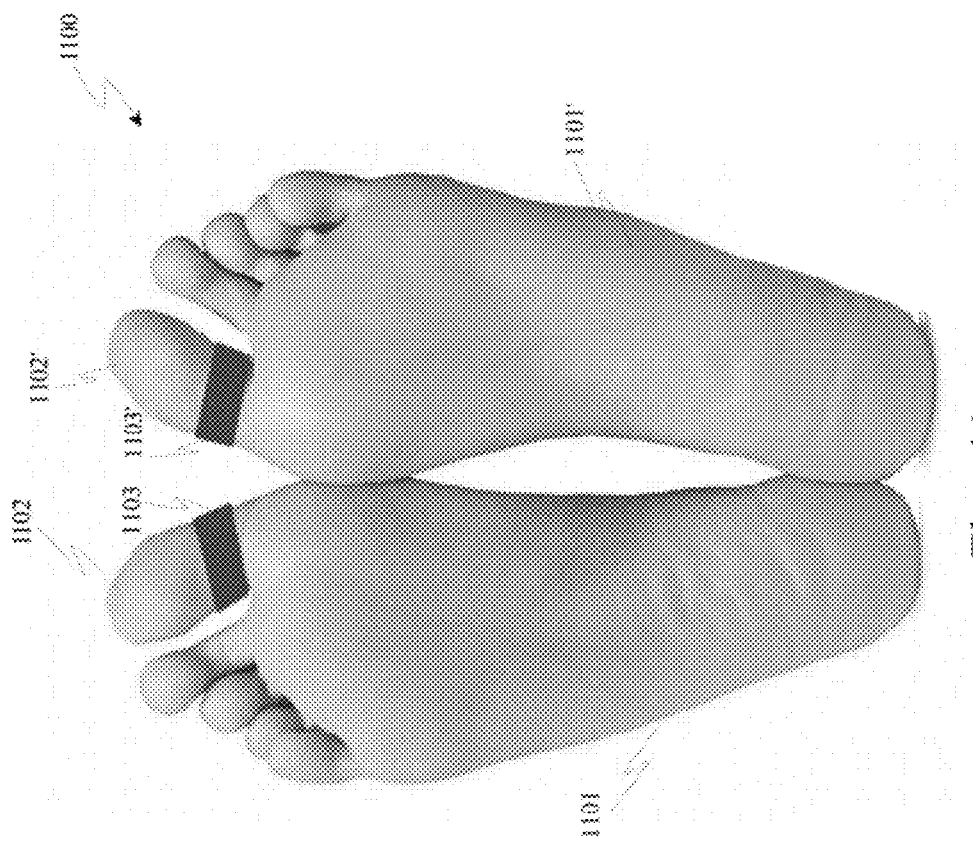
FIG. 11 illustrates how the biosensors are worn on a patient's or subject's great toes.
Figure 20:
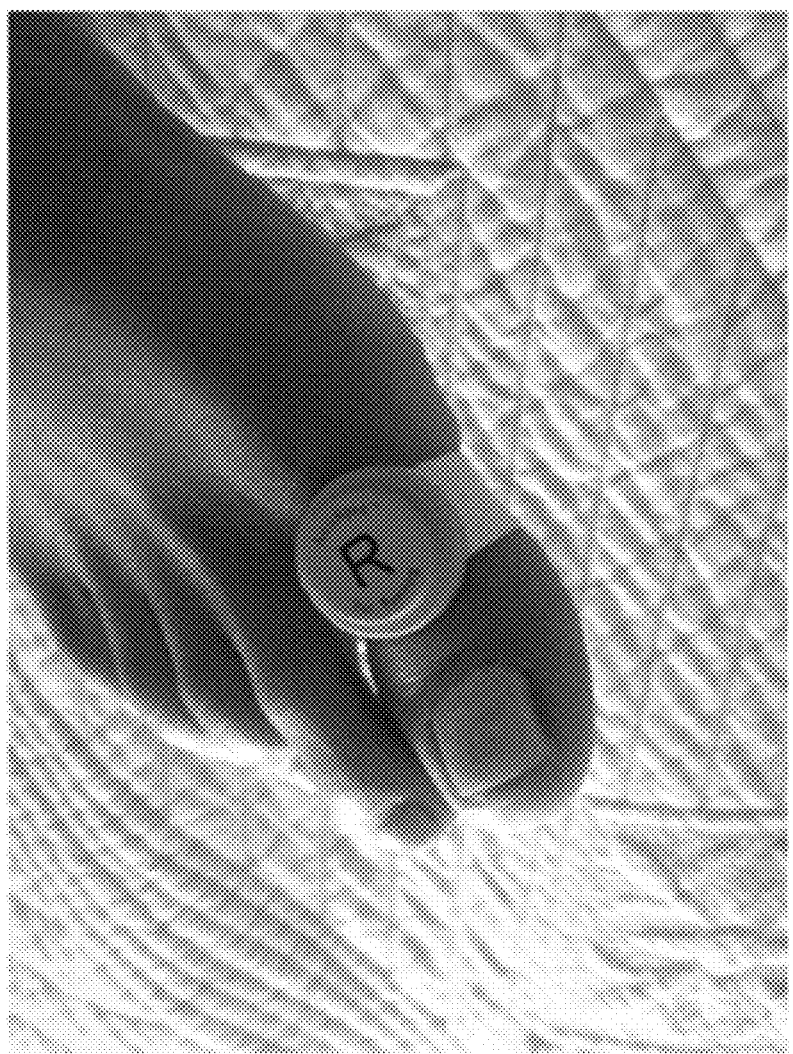
FIG. 20 shows a top, perspective view of at least one embodiment of the present invention as worn on a right great toe.

In general, biosensors (1103, 1103') according to the present invention are designed to be mounted on the great toes ("big toes") (1102, 1102') of one or both feet (1101, 1101'), and initially used for periodic limb movement (PLM) measurements during sleep, as shown in FIG. 11 (bottom of foot view) and in FIG. 20 (top of foot perspective view).

According to one aspect of the present invention, the inventor discovered that mounting the biosensors on the great toes provides maximum sensitivity for the detection of tibialis anterior muscle contractions. The tibialis anterior muscle is disposed along the front of the lower half of the human leg (front of the shin), not part of the foot, per se. Periodic limb movements in sleep (PLMS) are characterized by contraction of the tibialis anterior muscle in a periodic fashion. The contractions of the muscle occur for 0.5 to 10 seconds in duration, and are spaced between 5 to 90 seconds apart. A minimum of four (4) consecutive PLMs must occur before a PLM sequence is defined (i.e., counting begins only when four (4) PLMs are detected in succession and the total count of those PLMs in the sequence includes the initial four (4) movements).

The use of electromyography (EMG) is the "gold standard" for measuring PLMs in a sleep laboratory setting. Electrodes are typically placed bilaterally (both legs) over the tibialis anterior muscle and movements are recorded and scored using sophisticated software. Visually, contraction of tibialis anterior muscle initially causes the big toe to move followed by dorsiflexion of the ankle. The present inventor discovered that an accelerometer attached to the great toe can be used to indirectly measure contraction of the tibialis anterior muscle.

Many actigraphs marketed for sleep movement recording and analysis require the user to wear the prior art device on the ankle. This does not give the device the benefit of detecting the smaller movements in which the big toe moves without dorsiflexion of the ankle. Thus, these devices cannot sense small contractions of the tibialis anterior muscle.

Therefore, to achieve increased sensitivity, biosensors according to the present invention are worn on the big toe of each foot. This positioning provides the benefit of sensing small movements of the big toe, hence small contractions of the tibialis anterior muscle.

Device Packaging.

Figure 19:
FIG. 19 illustrates two embodiments according to the present invention, one utilizing an elastic fabric strip for the ring or band portion, and the other utilizing a flexible synthetic or plastic rubber-like material for the band portion molded integrally to the housing portion.

Turning to FIG. 1, one example embodiment of an electronics module according to the present invention for the biosensors is in a general toe-ring configuration (1103, 1103') which has an elastic band portion (1111) defining a space (1110) through which a human toe may be disposed, and a housing portion (1112). The housing portion (1112) defines an interior cavity (1114) within which the electronics are housed, and according to this exemplary embodiment, there is an indicator orifice through which a portion of the contents (1113) can be viewed, such as an indicator area. Generally, the electronics are comprised of a circular printed circuit board ("PCB"), a "coin" shaped battery (e.g. watch battery, hearing aid battery, etc.), and a battery holder, contained within a carrier, all of which are disposed in the housing portion (1112), which is fabricated in one embodiment of flexible form-fitting plastic. The elastic band portion is worn around the big toe, which couples the contained electronics to the movement of the toe. The elastic band portion may be fabricated of a length of elastic fabric, flexible plastic, synthetic rubber as shown in FIGS. 19(a) and (b), respectively. A prototype biosensor constructed according to the present invention may have a thickness of approximately 4.9 mm and a diameter of approximately 16.45 mm. Additional details of the housing and the circuitry are provided in subsequent paragraphs.

Physician/Patient Usage Model.

The physician/patient usage mail-in model is similar to that of the earlier version of the biosensor, as described in the foregoing paragraphs. However, in the case of the toe band embodiment, the "return card" would not be present or needed. The patient would simply remove the toe bands and insert the bands into the return envelope. All other aspects of the usage model apply similarly.

Optical Activation.

In the newer design and embodiments according to the present invention, there is no pull-tab for activation of the unit by the patient or user. Instead, embodiments according to the present invention are activated by light when the user removes each device from a light-proof outer packaging, such as metalized mylar envelop or other light-proof box, sleeve, tube, etc. The user will be instructed to not remove the devices from the outer packaging until they are ready to apply the devices to the subject's toes.

Multi-Night Operation.

In at least one exemplary embodiment of the biosensor according to the present invention, the biosensor electronics contain 128K bytes of non-volatile memory which enables the device to store up to 120 hours (5-days) worth of activity data at 0.5 sec intervals, using the sensing and storage logical process set forth herein. The biosensor device can be worn continuously during the entire 120-hour period, or removed during the day and reapplied each evening for up to five evenings. For sleep movement analysis, the bands are typically applied at night and removed in the morning for a five (5) night period.

Accelerometer and Sensitivity and Sampling Logical Processes.

The accelerometer sensitivity of the device used in at least one prototype design and test is 0.10 g (g=9.8 m/s$^2$) with a triaxial accelerometer (XYZ).

According to one logical process according to the present invention, samples are actually read by the microprocessor from the accelerometer device in a numeric (scalar or real) value. Instead, the circuit is designed and configured such that the accelerometer component interrupts the sleeping microprocessor if acceleration exceeds a threshold that is programmed into the accelerometer at initialization time. This allows the microprocessor to sleep while detected movements fall below a threshold, thereby saving power until a movement above the threshold is detected by the accelerometer device. Then, upon interrupt, the microprocessor leaves the sleep mode, stores a mark in memory (more details later), and returns to a low-power sleep mode. More details of the exemplary logical embodiments are provided in subsequent paragraphs.

Circuitry Details.

Figure 18:
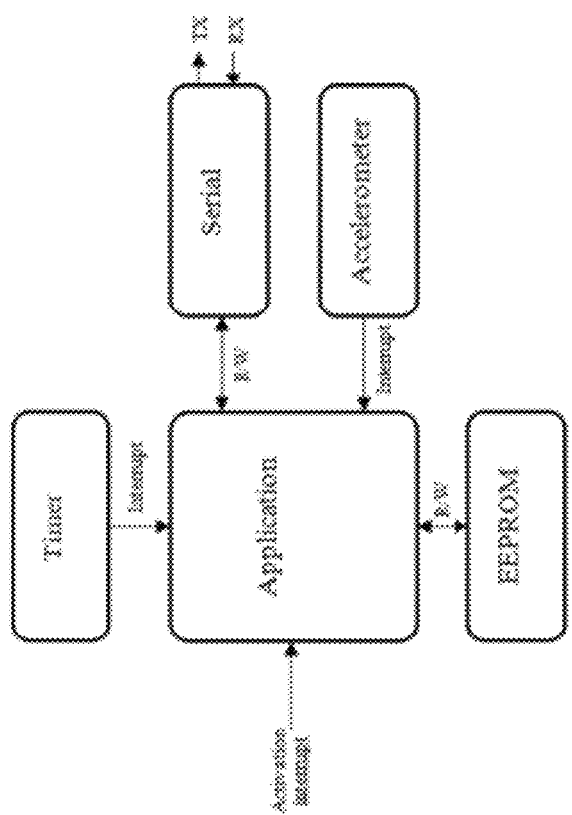
FIGS. 18(a) and 18(b) provide an exemplary embodiment hardware and software architecture and layering/hierarchy.
Figure 18:
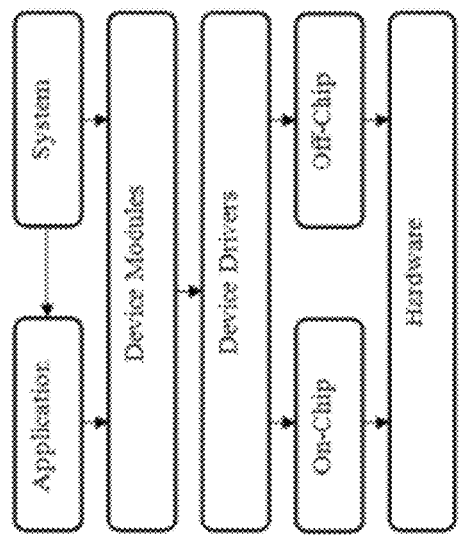

A generalized architecture of functionality, including hardware circuitry and firmware or software functions, is shown in FIG. 18(a), including a timer (can be on-board MCU timer, software timer, etc.), serial I/O (can be on-board MCU communications port or external I/O device, such as RS232, USB, WiFi, etc.), non-volatile memory devices (EEPROM, battery-backed RAM, etc.), and the application program(s) performed by a processor. FIG. 18(b) shows a layered architecture according to at least one embodiment of the invention in which the hardware components (on-chip and off-chip) are controlled by device drivers, which are controlled by device modules, which in turn are utilized by one or more application programs and optionally an operating system.

Figure 14:
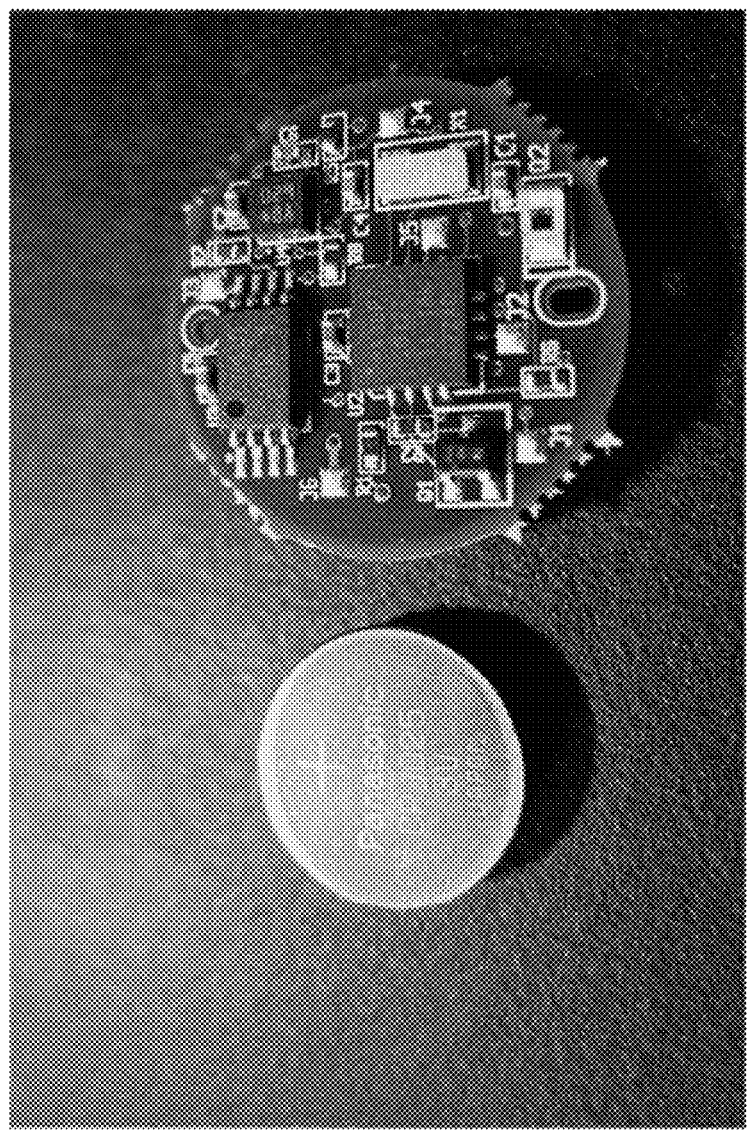
FIG. 14 shows a prototype electronics module and battery according to the present invention.

Referring now to FIG. 14, according to at least one exemplary embodiment (1122) according to the present invention, there are two main circuit groups of components, one for the biosensor device and the other for communications to the external world. The biosensor device includes the electronics module (PCB, battery, battery holder) that resides within a housing that is worn by the user on a big toe. The "communication board" is typically larger piece of hardware connected to the host PC (at the factory) and includes a universal asynchronous receive/transmit (UART) to Universal Serial Bus (USB) conversion integrated circuit (IC). In other embodiments, wireless networking such as Zigby, Bluetooth, and WiFi may be employed. Other communications protocols can be implemented in other embodiments, of course.

In this exemplary embodiment, the biosensor device hardware is comprised of:
1. A 16 MHz microcontroller (MCU) with 2 KB flash memory and 128B RAM (Texas Instrument's MSP430F2012)
2. Non-volatile device EEPROM memory (128 KB) (Atmel AT24C1024B)
3. +/−2 g accelerometer (Bosch Sensortec BMA250)
4. a light sensor
5. a 3V lithium coin battery and holder The communication board hardware is comprised of:
1. a USB-to-serial transceiver
2. Mini-USB connector
3. Voltage regulator (5V to 3.3 v)
4. Alignment and spring-loaded pogo pins for interfacing to device board (GND, 3.3V, TX, RX, JTAG DAT/CLK)

Regarding a power source, a button battery is sufficient for at least the foregoing circuit configuration. Other embodiments may include rechargeable batteries, which are charged by an array of optional charging devices, including but not limited to inductive chargers, solar chargers, and plug-in chargers.

Housing Details.

Figure 13:
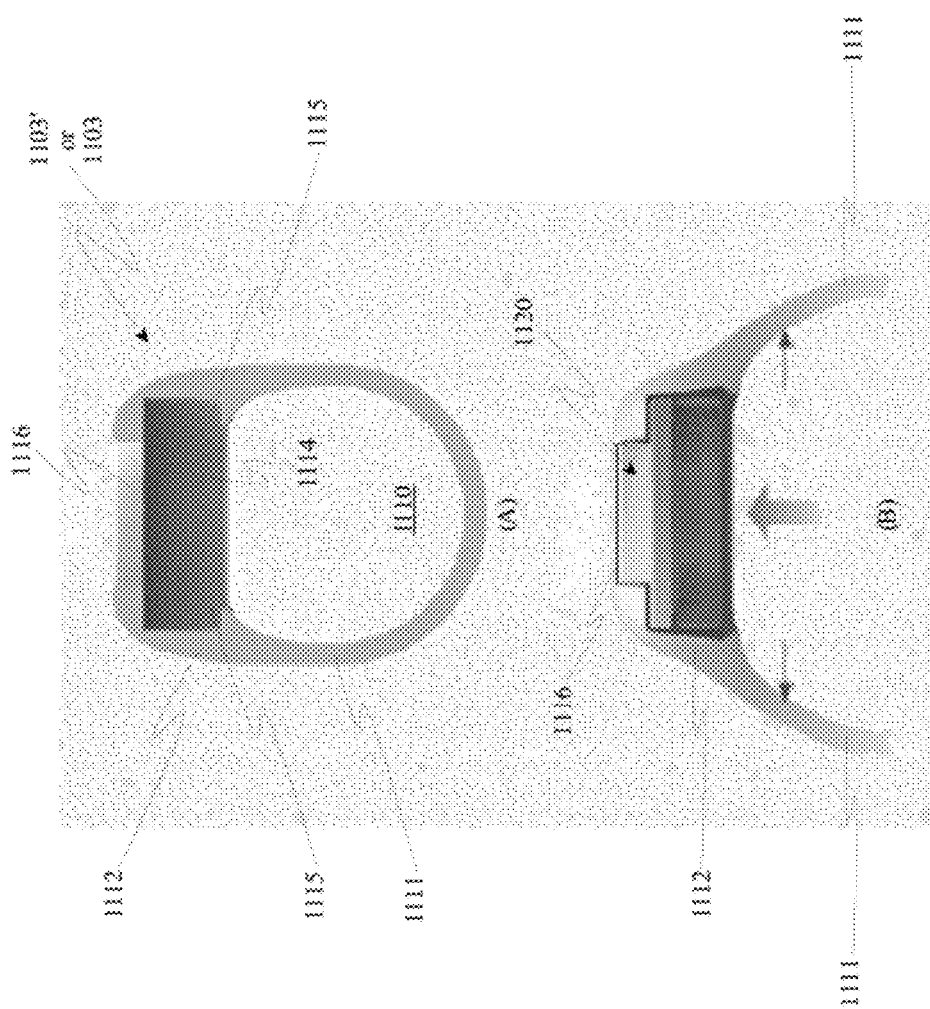
FIG. 13 provides a cross-sectional view of the interior of one embodiment of the housing, as well as an illustration of the insertion and removal of the stack-up of components.

Referring now to FIG. 13a, a cross-sectional view of the housing (1112) and band (1111) according to the at least one exemplary embodiment are shown, which provides a view of the cavity (1114) into which the electronics may be received and held. The indicator orifice (1116) is optional in this embodiment, and allows a portion of the electronics contained within (or another part) to be viewed, such as a disc indicating left or right toe association. In this embodiment, the cavity (1114) is substantially circular or cylindrical in shape and volume, and the indicator orifice (1116) has a sufficiently smaller diameter than that of the cavity so as to prevent the electronic contents from escaping through the orifice. Further, a retention shoulder (1115) is disposed, such as an annular shoulder (shown), at the portion of the cavity (1114) towards the band portion (1111), which is also sufficiently reduced in diameter (compared to the diameter of the cavity) to reliably retain the electronics.

To assemble the biosensor, a light force is applied outwardly on the band portion (1111), which causes the flexible material of the housing portion to stretch open as shown in FIG. 13b, such that the electronics (1120) may be disposed into the cavity with light force from the band space (1110) towards the orifice (1116). Then, the spreading force is removed, thereby allowing the resilient nature of the housing material to return to its normal shape and size, wherein the shoulder then engages the electronics to retain them in the cavity. Removal of the electronics from the housing portion is through a simple reversal of these steps.

It should be recognized by those skilled in the art that, while the expanding shoulder feature of this embodiment is novel, other methods of retention of the electronics are available, as well, such as snap fitting, friction retention, threading, gluing, etc. These embodiments would fall within the spirit and scope of the present invention, as well.

Figure 12:
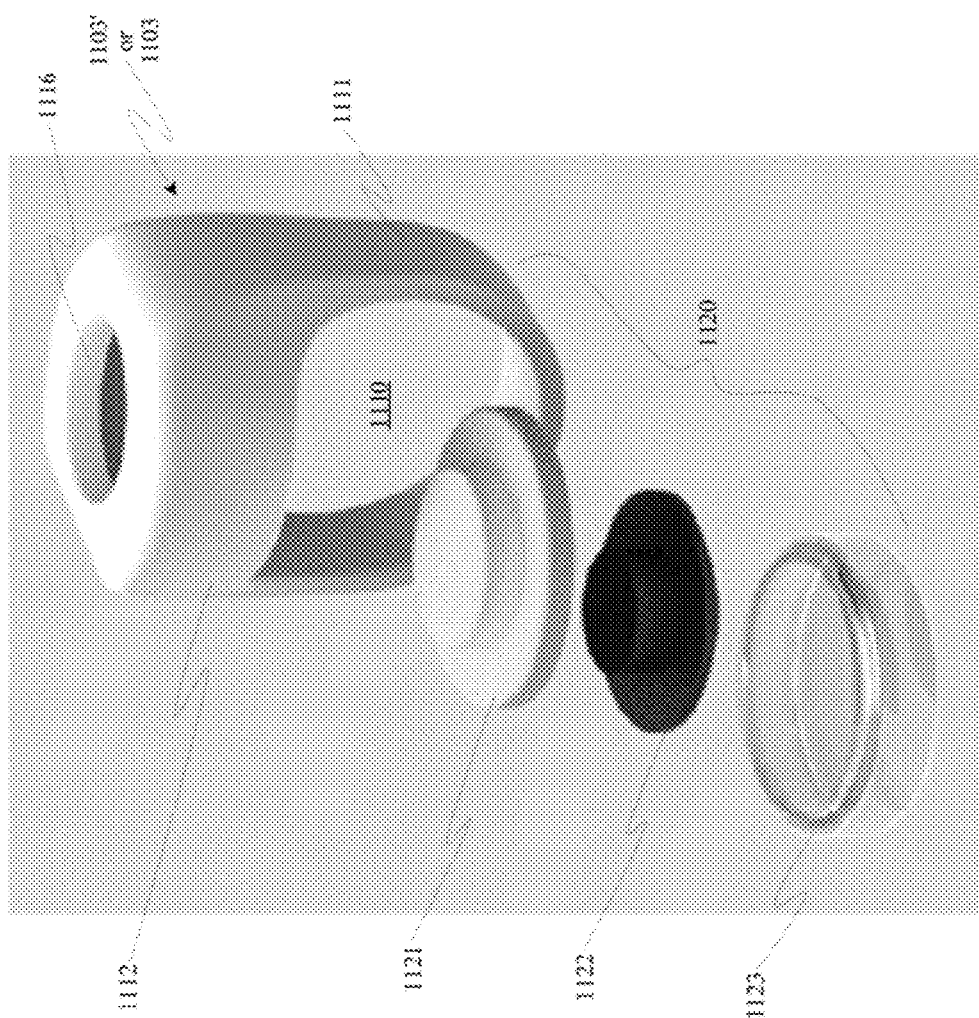
FIG. 12 sets forth a stack-up of components to house the biosensor's electronics.

Referring next to FIG. 12, a stack-up of components to house the electronics (1122) is shown. In this embodiment, the electronics (1122) are disposed into a dish-like container (1123), and then covered with a top (1121) to produce an encapsulated arrangement, which is then disposed into the cavity of the housing (1112) as previously described. The top cover (1121) may be provided with useful indicia, such as an "L" or "R", to guide the user for right or left foot use. In other embodiments, this top may be clear or partially transparent to allow an LED to be visible, or to provide access to an IrDA port, etc.

Logical Processes.

The microcontroller is provided with firmware, which when executed by the microcontroller, implements logical processes according to the present invention. The logical processes are broken down into two main areas: device and host. The device logical processes reside, according to at least one embodiment, on the device MCU within the module that is worn by the user and it performs activation, communication with a host computer, low-power management, and recording movement events by the accelerometer to the non-volatile memory. The device logical process is further sub-organized into three (3) primary modes of operation: administration (admin), standby mode, and active mode.

Figure 15:
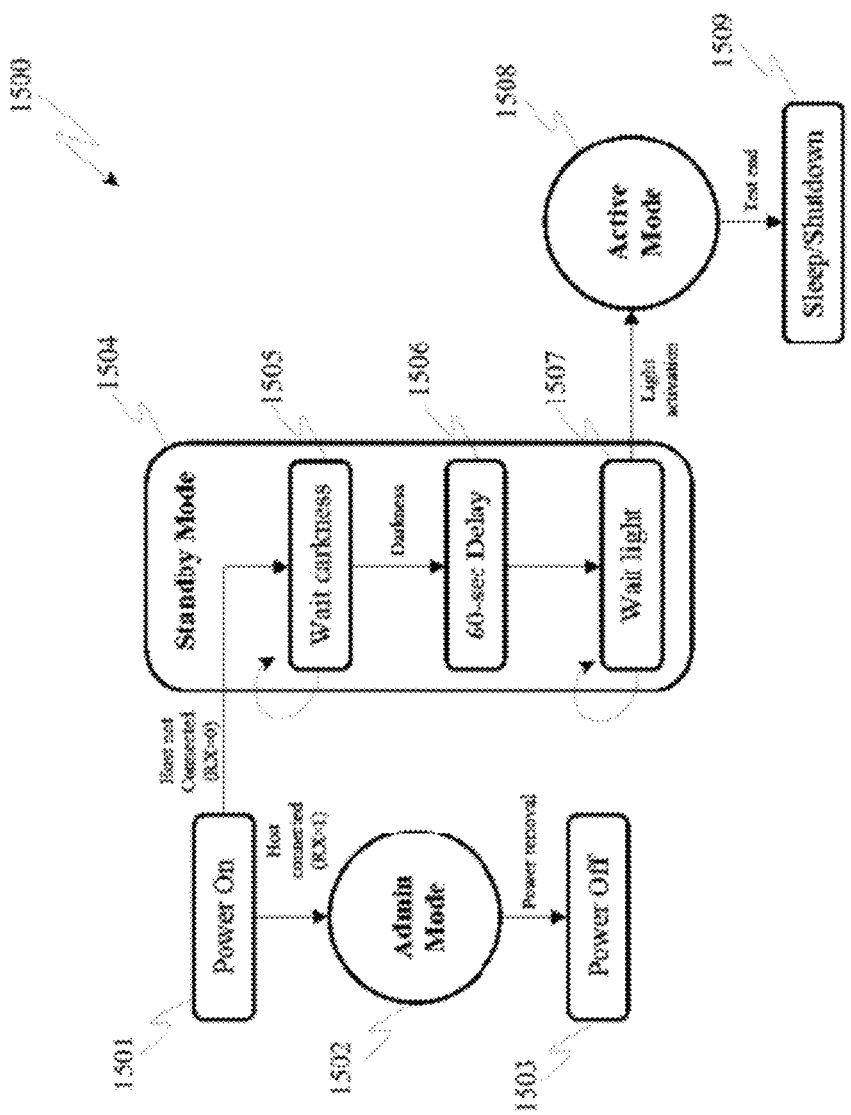
FIGS. 15 and 16 illustrate logical processes according to the present invention.

In this example logical process embodiment (1500) as illustrated in FIG. 15, responsive to power-up (1501) of the biosensor circuitry (e.g. inserting a battery, etc.), if the receive (RX) line is high (logical 1) to indicate that the device is connected to the communication board, then the device logical process enters admin mode (1502) until power-off (1503). In the admin mode, the host computer may issue commands to the biosensor's MCU.

If upon device power-up (1501) the RX line is low (logical 0), then the device logical process enters the standby mode (1504). In standby mode, the device logical process first waits for the light detector to sense darkness (1505) (e.g. transition of the device from outside the light-protected outer packaging to being inside the light-protected outer packaging). Responsive to sensing darkness, the MCU waits (1506) for approximately sixty (60) seconds and then waits (1507) for an interrupt from the light activation circuit. The sequence of steps within standby mode is to provide time for manufacturing assembly personnel to assemble and package the toe bands after the batteries have been inserted.

Still referring to the exemplary embodiment according to the invention, during standby mode while the device is waiting to be exposed to light for activation, there is minimal current drawn from the battery, thus giving the device a particularly long shelf life of approximately 2 years or more.

Upon opening the light-proof bag by the user, the light activation circuit will produce an interrupt to the MCU, which forces the MCU out of lower-power sleep mode and into the active mode (1508). In active mode, the device logical process collects and stores acceleration movement events for 120 hours. At the end of the 120-hour period, the device logical process places the MCU back into sleep mode (1509).

Figure 16:
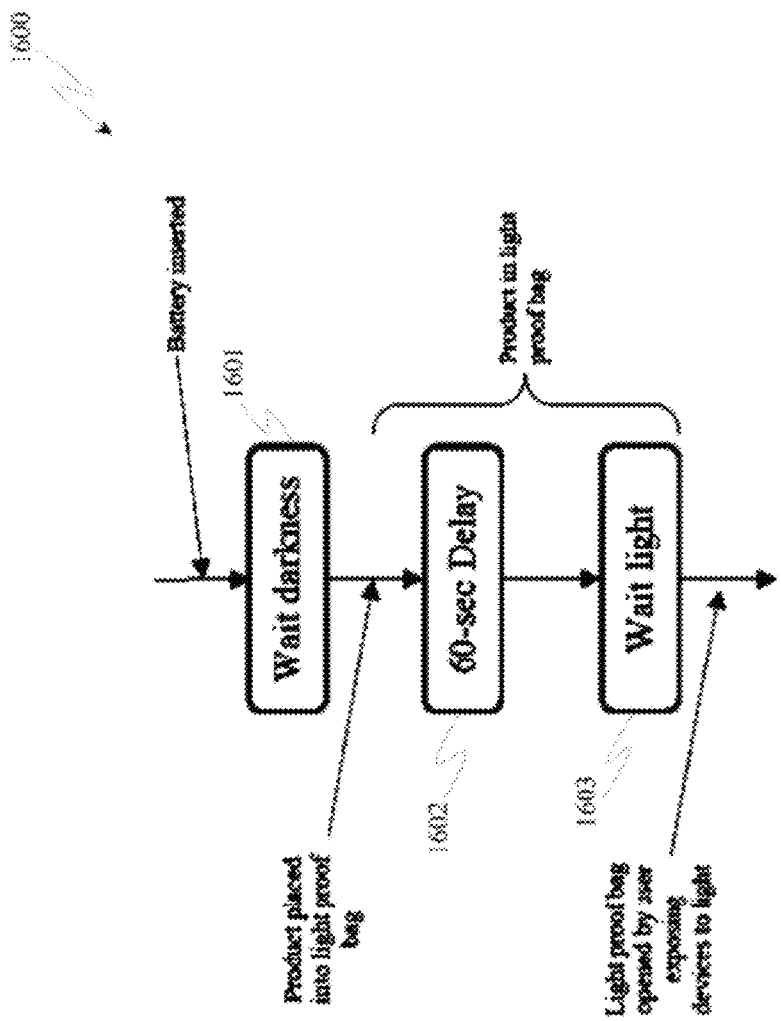

FIG. 16 illustrates in more detail the logical process (1600) from when the product is placed into the light proof bag to when it is removed (1601, 1602, 1063).

In active mode of this exemplary embodiment, the accelerometer is programmed to interrupt the MCU only when movement exceeds a pre-determined sensitivity threshold. A 2 Hz (500 ms period) timer is triggered within the device logical process, which determines whether or not movement (interrupt) occurred within that 500 ms window.

Figure 17:
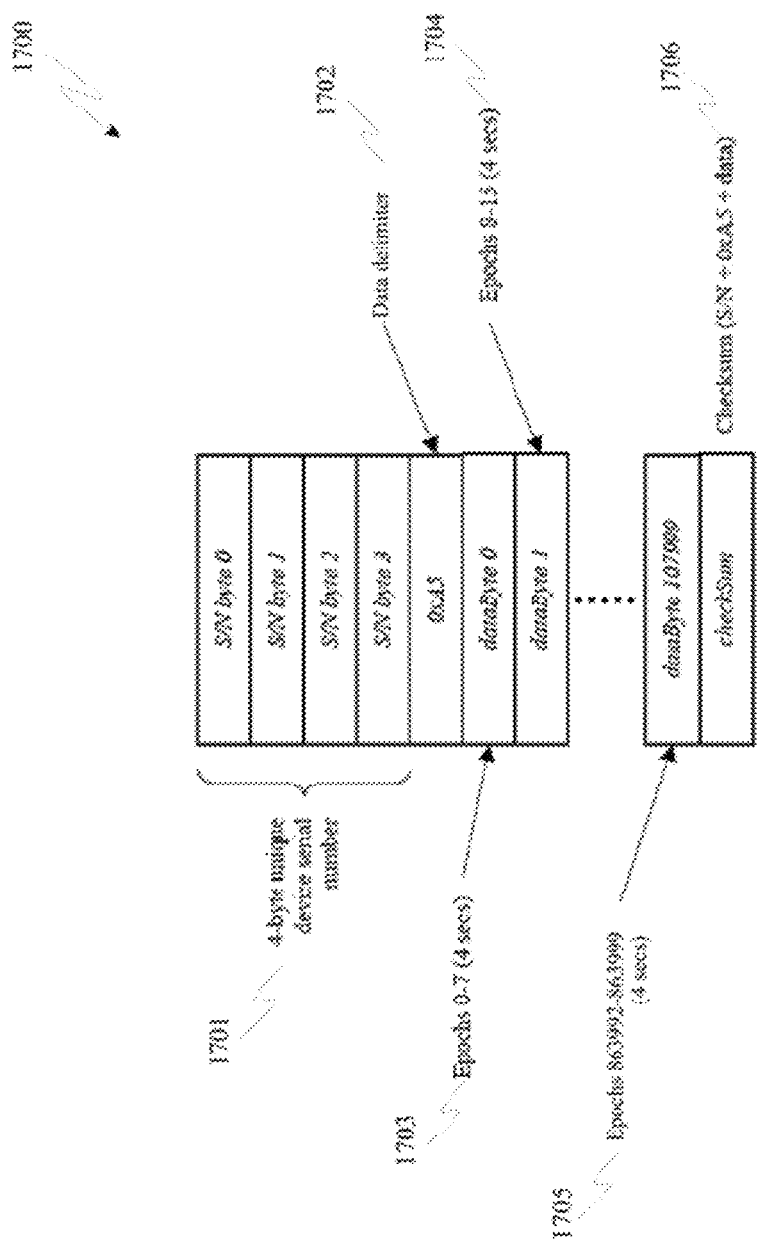
FIG. 17 depicts a data structure according to the present invention.

The non-volatile memory element in the biosensor in this exemplary embodiment is a 128 KB low-power serial electrically-erasable programmable read-only memory (EEPROM) device. To support a 5-day (120-hour) recording time, each bit in memory is treated as a 0.5-second "epoch" or sampling window. 108000 bytes are required to support this storage requirement (108000 bytes*8 bits/byte=5 days*24 hours/day*60 min/hr*60 sec/min*2 Hz=864000 bits), as shown in FIG. 17 in the data structure diagram (1700). A bit value of '1' means that one or more movement interrupts occurred within that 0.5-second window. A bit value of '0' means no movement occurred. In this manner, the device logical process optimizes memory usage, which in turn reduces memory size and power consumption, and which avoids using battery power to read actual acceleration values by the MCU from the accelerometer. By avoiding recording of the intensity of movements (e.g. accelerometer values), but rather recording a mark into memory only if a movement occurred within each 0.5-second period that exceeded the pre-determined acceleration sensitivity threshold, considerable power savings and memory size reduction are realized. For example, in this embodiment, the accelerometer is programmed to a 32 Hz sample rate (64 Hz bandwidth) with a 0.10 g sensitivity threshold, where 1 g=9.8 m/s$^2$.

In this exemplary memory structure, a four-byte serial number (1701) is recorded, followed by a data delimiter value, followed by the epoch bits (1703, 1704, 1705) which were previously described, and ended by a checksum (1706) to ensure data integrity.

Host Logical Processes.

The host logical processes may be realized as software or firmware executed by a computer, such as by an application program coupled to and executed by a personal computer (PC). The host logical processes communicate with the communication board via a serial (COM) port. The host logical process is, in one exemplary embodiment, in the form of a Graphical User Interface (GUI) which enables an authorized user (lab technician, nurse, manufacturing technician, etc.) to perform administrative commands such as erase, download, and program device serial number.

Data is downloaded from the biosensor by the host computer in binary form and includes a checksum for error detection in this example embodiment. The host computer may also be configured to analyze and score the movement data as well as producing a human-readable report, such as a portable document format (PDF) report. The report consists, in at least one embodiment, of graphs and statistical data necessary to interpret the movement analysis over the sampling 120-hour period.

Other Uses

It should be noted that the example embodiments and manners of usage do not define the full scope of the present invention, but provide an illustration of how the invention may be applied to a medical art which requires or is enhanced by measurement of limb movements. Other medical arts, including, but not limited to, the following examples may benefit as well:

(a) cardiology studies may be remotely and conveniently conducted on patients by providing a heart monitor version of the biosensor which can be used on the chest, wrist, or neck, such as during normal daily activities;

(b) other forms of sleep disorders, such as sleep apnea may be studied by providing a sound monitor with or without a movement monitor;

(c) nocturnal hypoglycemia may be studied in diabetics by studying shifts in limb movement patterns;

(d) body position may be sensed and recorded during sleep or another activity; and (e) neurological studies on stroke and seizure-prone patients can be performed using variations of the biosensor patch, including diseases such as Parkinson's Disease and Tourettes Syndrome.

For these reasons, the full scope and spirit of the present invention should be ascertained from the following claims.

I claim:

1. A biosensor for detection of limb movement and collection of biosensor data comprising:

a biosensor housing having a ring portion and a housing portion, the ring portion defining a passage way for receiving a toe, finger, or other appendage; and an electronics sensor package disposed within or onto the housing portion of the biosensor housing having a power source, a movement processor, an activator, a data memory device, and a communications interface for transmitting data, wherein the movement processor is powered by the power source responsive to the activator, wherein movement of an appendage received in the ring portion is detected and recorded into the data memory device by the movement processor, wherein the activator comprises at least a light sensor, and wherein the recorded movement in the data memory device is selectively transmittable via the communications interface.

2. The biosensor as set forth in claim 1 wherein the ring portion is proportioned to receive a human great toe, and wherein the movement processor is configured to respond to and detect dorsiflexion of the human great toe in response to contraction of a *tibialis* anterior muscle of a wearer of the biosensor.

3. The biosensor as set forth in claim 1 wherein the movement processor comprises a microcontroller and at least one accelerometer.

4. The biosensor as set forth in claim 3 wherein the microcontroller is configured to assume an active processing mode responsive to receiving an interrupt signal from the at least one accelerometer.

5. The biosensor as set forth in claim 4 wherein the at least one accelerometer is configured to post an interrupt to the microcontroller only upon sensing acceleration above a pre-determined acceleration threshold.

6. The biosensor as set forth in claim 5 wherein the microcontroller is further configured to make a mark in the data memory records responsive to receiving the interrupt, and to assume an inactive processing mode after making the mark.

7. The biosensor as set forth in claim 6 wherein reading of a data value by the microcontroller from the accelerometer is avoided.

8. The biosensor as set forth in claim 7 wherein the inactive processing mode consumes less power by the microcontroller than the active processing mode.

9. The biosensor as set forth in claim 1 wherein the movement processor is configured to sense a dark period of at least a minimum length of time, and responsive to the detection of the dark period, to assume an inactive processing mode until the activator senses light, responsive to which the movement processor assumes an active processing mode, wherein the inactive processing mode consumes less power by the microcontroller than the active processing mode.

10. The biosensor as set forth in claim 1 wherein the movement processor is configured to enter an administrative mode upon sensing a pre-determined pattern of light and dark periods.

11. The biosensor as set forth in claim 1 wherein the ring portion comprises an elastic portion which provides a stretched state for receiving wearer's appendage, and further provides a released configuration state to retain the biosensor on the received appendage.

12. The biosensor as set forth in claim 1 wherein the housing portion defines a cavity into which the electronics sensor package is received and retained.

13. The biosensor as set forth in claim 12 wherein the cavity further allows removal of the electronics sensor package.

14. The biosensor as set forth in claim 12 wherein the housing portion comprises an elastic portion which provides a stretched state for receiving the electronics sensor package, and further provides a released state for retaining the electronics sensor package.

15. The biosensor as set forth in claim 1 wherein the housing portion comprises an indicator window through which a portion of the electronics sensor package is visible to a user.

16. The biosensor as set forth in claim 15 wherein the indicator window comprises an appendage indicator.

17. The biosensor as set forth in claim 15 wherein the activator comprises a light sensor which is configured to sense an ambient light level through the indicator window.

* * * * *